US008747331B2

(12) United States Patent
Luginbuhl et al.

(10) Patent No.: US 8,747,331 B2
(45) Date of Patent: Jun. 10, 2014

(54) VARIABLE ANGLE GUIDE HOLDER FOR A BIOPSY GUIDE PLUG

(75) Inventors: Christopher Luginbuhl, Toronto (CA); Nathan Bluvol, Toronto (CA)

(73) Assignee: Hologic, Inc., Marlborough, MA (US)

( * ) Notice: Subject to any disclaimer, the term of this patent is extended or adjusted under 35 U.S.C. 154(b) by 652 days.

(21) Appl. No.: 12/822,110

(22) Filed: Jun. 23, 2010

(65) Prior Publication Data

US 2011/0152714 A1 Jun. 23, 2011

Related U.S. Application Data

(60) Provisional application No. 61/213,594, filed on Jun. 23, 2009.

(51) Int. Cl.
*A61B 10/00* (2006.01)

(52) U.S. Cl.
CPC .................................... *A61B 10/00* (2013.01)
USPC ........................................................ 600/562

(58) Field of Classification Search
USPC .................................... 600/562–568; 606/130
See application file for complete search history.

(56) References Cited

U.S. PATENT DOCUMENTS

| | | | | |
|---|---|---|---|---|
| 3,115,140 | A * | 12/1963 | Volkman | 607/116 |
| 4,503,844 | A | 3/1985 | Siczek | |
| 4,552,346 | A | 11/1985 | Schnelle et al. | |
| 4,572,203 | A | 2/1986 | Feinstein | |
| 4,733,661 | A * | 3/1988 | Palestrant | 606/108 |
| 4,825,162 | A | 4/1989 | Roemer et al. | |
| 4,930,516 | A | 6/1990 | Alfano et al. | |
| 4,930,525 | A * | 6/1990 | Palestrant | 128/898 |
| 4,943,986 | A | 7/1990 | Barbarisi | |
| 4,989,608 | A | 2/1991 | Ratner | |
| 5,014,968 | A | 5/1991 | Lammers et al. | |
| 5,047,036 | A * | 9/1991 | Koutrouvelis | 606/130 |
| 5,072,721 | A | 12/1991 | Weiler et al. | |
| 5,096,216 | A | 3/1992 | McCalla | |
| 5,154,179 | A | 10/1992 | Ratner | |

(Continued)

FOREIGN PATENT DOCUMENTS

| | | |
|---|---|---|
| CN | 1640139 A | 7/2005 |
| CN | 101601266 A | 12/2009 |

(Continued)

OTHER PUBLICATIONS

PCT/CA10/000973, International Preliminary Report on Patentability, Jan. 4, 2012.

(Continued)

*Primary Examiner* — Sean Dougherty
*Assistant Examiner* — Michael C Stout
(74) *Attorney, Agent, or Firm* — Lando & Anastasi, LLP

(57) ABSTRACT

Apparatus and methods are described as relating to a variable angled guide plug holder for use in interventional procedures. In an exemplary embodiment, a variable angled guide plug holder for use in interventional procedures is provided, including a guide plug holder for receiving an angular determination fixture, the guide plug holder movable relative to the angular determination fixture between a plurality of positions, each position providing a different angle of insertion relative to a point of origin on the angular determination fixture, and plate plug engaged with the angular determination fixture wherein the plate plug is insertable into a guide plate aperture of a guide plate for use in an interventional procedure.

19 Claims, 19 Drawing Sheets

(56) References Cited

U.S. PATENT DOCUMENTS

| | | | | |
|---|---|---|---|---|
| 5,196,019 A | * | 3/1993 | Davis et al. | 606/130 |
| 5,297,551 A | | 3/1994 | Margosian et al. | |
| 5,308,352 A | * | 5/1994 | Koutrouvelis | 606/130 |
| 5,426,685 A | | 6/1995 | Pellegrino et al. | |
| 5,548,218 A | | 8/1996 | Lu | |
| 5,569,266 A | | 10/1996 | Siczek | |
| 5,575,798 A | * | 11/1996 | Koutrouvelis | 606/130 |
| 5,590,653 A | | 1/1997 | Aida et al. | |
| 5,590,655 A | | 1/1997 | Hussman | |
| 5,594,337 A | | 1/1997 | Boskamp | |
| 5,678,549 A | | 10/1997 | Heywang-Koebrunner et al. | |
| 5,682,098 A | | 10/1997 | Vij | |
| 5,682,890 A | | 11/1997 | Kormos et al. | |
| 5,706,812 A | | 1/1998 | Strenk et al. | |
| 5,744,958 A | | 4/1998 | Werne | |
| 5,782,764 A | | 7/1998 | Werne | |
| 5,817,023 A | | 10/1998 | Daft | |
| 5,855,554 A | | 1/1999 | Schneider et al. | |
| 5,868,673 A | | 2/1999 | Vesely | |
| 5,868,757 A | | 2/1999 | Koutrouvelis | |
| 5,944,023 A | | 8/1999 | Johnson et al. | |
| 6,066,102 A | | 5/2000 | Townsend et al. | |
| 6,091,985 A | | 7/2000 | Alfano et al. | |
| 6,159,221 A | | 12/2000 | Chakeres | |
| 6,163,616 A | | 12/2000 | Feldman | |
| 6,163,717 A | | 12/2000 | Su | |
| 6,174,291 B1 | | 1/2001 | McMahon et al. | |
| 6,201,392 B1 | | 3/2001 | Anderson et al. | |
| 6,229,145 B1 | | 5/2001 | Weinberg | |
| 6,281,681 B1 | | 8/2001 | Cline et al. | |
| 6,295,671 B1 | | 10/2001 | Reesby et al. | |
| 6,298,506 B1 | | 10/2001 | Heinold et al. | |
| 6,302,579 B1 | | 10/2001 | Meyer et al. | |
| 6,324,243 B1 | | 11/2001 | Edic et al. | |
| 6,334,067 B1 | * | 12/2001 | Brabrand | 600/427 |
| 6,421,454 B1 | | 7/2002 | Burke et al. | |
| 6,421,553 B1 | | 7/2002 | Costa et al. | |
| 6,437,567 B1 | | 8/2002 | Schenck et al. | |
| 6,446,286 B1 | | 9/2002 | Karmalawy | |
| 6,459,923 B1 | | 10/2002 | Plewes et al. | |
| 6,498,489 B1 | | 12/2002 | Vij | |
| 6,521,209 B1 | | 2/2003 | Meade et al. | |
| 6,526,299 B2 | | 2/2003 | Pickard | |
| 6,591,128 B1 | | 7/2003 | Wu et al. | |
| 6,593,101 B2 | | 7/2003 | Richards-Kortum et al. | |
| 6,628,983 B1 | | 9/2003 | Gagnon | |
| 6,639,406 B1 | | 10/2003 | Boskamp et al. | |
| 6,640,364 B1 | | 11/2003 | Josephson et al. | |
| 6,675,037 B1 | | 1/2004 | Tsekos | |
| 6,697,652 B2 | | 2/2004 | Georgakoudi et al. | |
| 6,723,303 B1 | | 4/2004 | Quay | |
| 6,806,711 B2 | | 10/2004 | Reykowski | |
| 6,810,595 B2 | * | 11/2004 | Chan | 33/286 |
| 6,822,450 B2 | | 11/2004 | Klinge et al. | |
| 6,867,593 B2 | | 3/2005 | Menon et al. | |
| 6,904,305 B2 | | 6/2005 | Tsekos | |
| 6,922,859 B2 | | 8/2005 | Gagnon et al. | |
| 6,927,406 B2 | | 8/2005 | Zyromski | |
| 6,950,492 B2 | | 9/2005 | Besson | |
| 7,011,447 B2 | | 3/2006 | Moyers | |
| 7,020,314 B1 | | 3/2006 | Suri et al. | |
| 7,023,209 B2 | | 4/2006 | Zhang et al. | |
| 7,024,027 B1 | | 4/2006 | Suri et al. | |
| 7,024,711 B1 | | 4/2006 | Stasney et al. | |
| D533,278 S | | 12/2006 | Luginbuhl et al. | |
| 7,155,043 B2 | | 12/2006 | Daw | |
| 7,166,113 B2 | * | 1/2007 | Arambula et al. | 606/130 |
| 7,176,683 B2 | | 2/2007 | Reeder et al. | |
| 7,245,125 B2 | | 7/2007 | Harer et al. | |
| 7,245,694 B2 | | 7/2007 | Jing et al. | |
| D569,977 S | | 5/2008 | Luginbuhl et al. | |
| 7,373,676 B2 | | 5/2008 | Markovic et al. | |
| 7,379,769 B2 | | 5/2008 | Piron et al. | |
| 7,545,966 B2 | | 6/2009 | Lewin et al. | |
| 7,583,786 B2 | | 9/2009 | Jing et al. | |
| 7,656,993 B2 | * | 2/2010 | Hoernig | |
| 7,711,407 B2 | * | 5/2010 | Hughes et al. | 600/417 |
| 7,809,426 B2 | | 10/2010 | Kim et al. | |
| 7,881,428 B2 | | 2/2011 | Jing et al. | |
| 7,908,690 B2 | | 3/2011 | Luginbuhl et al. | |
| 7,925,328 B2 | * | 4/2011 | Urquhart et al. | 600/429 |
| 7,937,132 B2 | | 5/2011 | Piron et al. | |
| 7,970,452 B2 | | 6/2011 | Piron et al. | |
| 8,050,736 B2 | * | 11/2011 | Piron et al. | 600/415 |
| 8,155,417 B2 | | 4/2012 | Piron et al. | |
| 8,162,847 B2 | * | 4/2012 | Wale et al. | 600/562 |
| 8,162,848 B2 | * | 4/2012 | Hibner et al. | 600/562 |
| 8,162,849 B2 | * | 4/2012 | Deshmukh et al. | 600/562 |
| 8,241,301 B2 | * | 8/2012 | Zhang et al. | 606/130 |
| 8,290,569 B2 | | 10/2012 | Piron et al. | |
| 8,292,824 B2 | * | 10/2012 | Okada | 600/564 |
| 8,298,245 B2 | * | 10/2012 | Li et al. | 606/130 |
| 2001/0011394 A1 | | 8/2001 | Heimbrock et al. | |
| 2001/0039378 A1 | | 11/2001 | Lampman et al. | |
| 2002/0035864 A1 | | 3/2002 | Paltieli et al. | |
| 2002/0056161 A1 | | 5/2002 | Falbo et al. | |
| 2002/0073717 A1 | | 6/2002 | Dean et al. | |
| 2002/0095730 A1 | | 7/2002 | Al-Kassim et al. | |
| 2002/0099264 A1 | | 7/2002 | Fontenot | |
| 2002/0131551 A1 | | 9/2002 | Johnson et al. | |
| 2002/0156365 A1 | | 10/2002 | Tsekos | |
| 2002/0164810 A1 | | 11/2002 | Dukor et al. | |
| 2002/0180442 A1 | | 12/2002 | Vij | |
| 2002/0193815 A1 | | 12/2002 | Foerster et al. | |
| 2003/0007598 A1 | | 1/2003 | Wang et al. | |
| 2003/0191397 A1 | | 10/2003 | Webb | |
| 2003/0194050 A1 | | 10/2003 | Eberhard et al. | |
| 2003/0199753 A1 | | 10/2003 | Hibner et al. | |
| 2003/0199754 A1 | | 10/2003 | Hibner et al. | |
| 2003/0206019 A1 | | 11/2003 | Boskamp | |
| 2004/0077972 A1 | * | 4/2004 | Tsonton et al. | 600/564 |
| 2004/0081273 A1 | | 4/2004 | Ning | |
| 2004/0183534 A1 | | 9/2004 | Chan et al. | |
| 2004/0216233 A1 | | 11/2004 | Ludwig et al. | |
| 2004/0220467 A1 | | 11/2004 | Bonutti | |
| 2005/0005356 A1 | | 1/2005 | Zacharopoulos et al. | |
| 2005/0033315 A1 | * | 2/2005 | Hankins | 606/129 |
| 2005/0059877 A1 | | 3/2005 | Falbo | |
| 2005/0080333 A1 | * | 4/2005 | Piron et al. | 600/417 |
| 2005/0104591 A1 | | 5/2005 | Qu et al. | |
| 2005/0228267 A1 | | 10/2005 | Bulkes et al. | |
| 2005/0267373 A1 | * | 12/2005 | Lee | 600/471 |
| 2006/0024132 A1 | | 2/2006 | Seman | |
| 2006/0026761 A1 | | 2/2006 | Falbo | |
| 2006/0122630 A1 | * | 6/2006 | Daum et al. | 606/130 |
| 2006/0133580 A1 | | 6/2006 | Vezina | |
| 2006/0221942 A1 | | 10/2006 | Fruth et al. | |
| 2006/0241408 A1 | | 10/2006 | Yakubovsky et al. | |
| 2007/0016003 A1 | | 1/2007 | Piron et al. | |
| 2007/0038144 A1 | * | 2/2007 | Hughes et al. | 600/562 |
| 2007/0039101 A1 | | 2/2007 | Luginbuhl et al. | |
| 2007/0050908 A1 | | 3/2007 | Kogan et al. | |
| 2007/0092059 A1 | | 4/2007 | Eberhard et al. | |
| 2007/0149878 A1 | * | 6/2007 | Hankins | 600/427 |
| 2007/0161935 A1 | | 7/2007 | Torrie et al. | |
| 2007/0167769 A1 | | 7/2007 | Ikuma et al. | |
| 2007/0233157 A1 | * | 10/2007 | Mark et al. | 606/130 |
| 2007/0238949 A1 | | 10/2007 | Wang et al. | |
| 2007/0255168 A1 | | 11/2007 | Hibner et al. | |
| 2007/0255170 A1 | * | 11/2007 | Hibner et al. | 600/564 |
| 2007/0276234 A1 | | 11/2007 | Shahidi | |
| 2008/0005838 A1 | | 1/2008 | Wan Fong et al. | |
| 2008/0033454 A1 | * | 2/2008 | Lukoschek et al. | 606/130 |
| 2008/0077005 A1 | | 3/2008 | Piron et al. | |
| 2008/0095421 A1 | | 4/2008 | Sun et al. | |
| 2008/0132785 A1 | * | 6/2008 | Piron et al. | 600/426 |
| 2008/0132912 A1 | * | 6/2008 | Shabaz | 606/130 |
| 2008/0216239 A1 | | 9/2008 | Luginbuhl et al. | |
| 2008/0230074 A1 | | 9/2008 | Zheng et al. | |
| 2008/0234569 A1 | | 9/2008 | Tidhar et al. | |
| 2008/0255443 A1 | * | 10/2008 | Piron et al. | 600/410 |
| 2008/0306377 A1 | | 12/2008 | Piron et al. | |
| 2009/0149738 A1 | | 6/2009 | Piron et al. | |
| 2009/0156961 A1 | * | 6/2009 | Tsonton et al. | 600/562 |

(56) References Cited

U.S. PATENT DOCUMENTS

| | | | |
|---|---|---|---|
| 2009/0216110 | A1 | 8/2009 | Piron et al. |
| 2009/0222229 | A1 | 9/2009 | Kakinami |
| 2009/0247861 | A1 | 10/2009 | Manus et al. |
| 2009/0270725 | A1 | 10/2009 | Leimbach et al. |
| 2009/0275830 | A1 | 11/2009 | Falco et al. |
| 2010/0041990 | A1* | 2/2010 | Schlitt et al. .................. 600/439 |
| 2010/0249595 | A1 | 9/2010 | Xu et al. |
| 2010/0280354 | A1* | 11/2010 | Zhang et al. .................. 600/411 |
| 2010/0324445 | A1* | 12/2010 | Mollere et al. ................ 600/564 |
| 2010/0324448 | A1* | 12/2010 | Mollere ........................ 600/567 |
| 2011/0034796 | A1 | 2/2011 | Ma et al. |
| 2011/0134113 | A1 | 6/2011 | Ma et al. |
| 2011/0152714 | A1 | 6/2011 | Luginbuhl et al. |
| 2011/0153254 | A1 | 6/2011 | Hartov et al. |
| 2011/0173753 | A1 | 7/2011 | Luginbuhl et al. |
| 2012/0172704 | A1 | 7/2012 | Piron et al. |
| 2013/0053684 | A1 | 2/2013 | Piron et al. |

FOREIGN PATENT DOCUMENTS

| | | |
|---|---|---|
| EP | 0396866 A2 | 11/1990 |
| EP | 0753758 A1 | 1/1997 |
| EP | 2445413 A1 | 5/2012 |
| EP | 2503934 A1 | 10/2012 |
| WO | 9608199 A1 | 3/1996 |
| WO | 01/28412 A1 | 4/2001 |
| WO | 02/39135 A2 | 5/2002 |
| WO | 2006017172 A1 | 2/2006 |
| WO | 2007070285 A2 | 6/2007 |
| WO | 2008064271 A2 | 5/2008 |
| WO | 2010078048 A2 | 7/2010 |
| WO | 2010148503 A1 | 12/2010 |
| WO | 2011014966 A1 | 2/2011 |
| WO | 2011134113 A1 | 11/2011 |
| WO | 2013001377 A2 | 1/2013 |

OTHER PUBLICATIONS

Piron, Cameron A., Hybrid Imaging Guidance System for Biopsy of the Breast, Thesis Paper, University of Toronto, 2001.
International Search Report for International Application No. PCT/CA2010/000973, mailed Oct. 1, 2010, 3 pages.
International Search Report for International Application No. PCT/CA2010/001228 mailed Oct. 2, 2011, 5 pages.
European Search Report mailed Mar. 1, 2012 for European Patent Application No. 07800538.6, 8 pages.
European Search Report for European Patent Application No. 07800538.6 mailed Mar. 1, 2012, 8 pages.
Palmer, Gregory, et al., "Optimal Methods for Fluorescence and Diffuse Reflectance Measurements of Tissue Biopsy Samples," Lasers in Surgery and Medicine, 30:191-200 (2002).
Kline, Nicole, et al., "Raman Chemical Imaging of Breast Tissue," Journal of Raman Spectroscopy, vol. 28, 119-124 (1997).
Manoharan, Ramasamy, et al., "Histochemical Analysis of Biological Tissues Using Raman Spectroscopy," Spectrochimica Acta Part A.52 (1996) 215-249.
Shafer-Peltier, K.E. et al. "Raman Microspectroscopic Model of Human Breast Tissue: Implications for Breast Cancer Diagnosis in Vivo" Journal of Raman Spectroscopy V.33 (2002).
Ntziachristos V., et al. "Concurrent MRI and Diffuse Optical Tomography of Breast After Indocyanine Green Enhancement," PNAS, Mar. 14, 2000, vol. 97, No. 6, 2767-2772.
Buadu, Ld, et al., Breast Lesions: Correlation of Contrast Medium Enhancement Patterns on MR Images with Histopathologic Findings and Tumor Angiogenesis.
Kriege, M., et al., "Efficacy of MRI and Mammography for Breast-Cancer Screening in Women with Familial or Genetic Predisposition," N Engl J Med 351:427-437 (2004).
Non-Final Office Action mailed Feb. 9, 2007 in U.S. Appl. No. 10/916,738.
Response to Feb. 9, 2007 Office Action in U.S. Appl. No. 10/916,738, Jul. 11, 2007.
Non-Final Office Action mailed Sep. 24, 2007 in U.S. Appl. No. 10/916,738.
Response to Sep. 24, 2007 Office Action in U.S. Appl. No. 10/916,738, Dec. 26, 2007.
Non-Final Office Action mailed Nov. 16, 2009 in U.S. Appl. No. 11/442,944.
Response to Nov. 16, 2009 Office Action in U.S. Appl. No. 11/442,944, May 17, 2010.
Non-Final Office Action mailed May 12, 2009 in U.S. Appl. No. 12/031,271.
Response to May 12, 2009 Office Action in U.S. Appl. No. 12/031,271, Nov. 12, 2009.
Final Office Action mailed Feb. 5, 2010 in U.S. Appl. No. 12/031,271.
Response to Feb. 5, 2010 Office Action in U.S. Appl. No. 12/031,271, Aug. 5, 2010.
Non-Final Office Action mailed Jan. 22, 2010 in U.S. Appl. No. 11/447,053.
Response to Jan. 22, 2010 Office Action in U.S. Appl. No. 11/447,053, Jul. 22, 2010.
International Search Report mailed Dec. 13, 2007 in International Application No. PCT/CA2007/001513.
International Preliminary Report on Patentability issued Mar. 3, 2009 in International Application No. PCT/CA2007/001513.
European Search Report mailed Jul. 30, 2009 in EP Application No. 09007010.3.
European Search Report mailed Oct. 16, 2009 in EP Application No. 09007010.3.
General Electric—Press Release—"GE Healthcare Introduces Ultrasound Fusion; New LOGIQ E9 Merges Real-time Ultrasound with CT, MR AND PET," Sep. 2, 2008, 2 pages.
International Preliminary Report of Patentability for International Application No. PCT/CA2010/001871 dated May 30, 2012, 1 page.
International Search Report and Written Opinion of the International Searching Authority for International Application No. PCT/CA2010/001871 dated Mar. 8, 2011, 9 pages.
M. Berger, "Image Fusion and Needle Guidance in Ultrasound", General Electric, Power Point Presentation, date unknown, 17 pages.
P. Mullen and C. Owen, "MR, Ultrasound Fusion: Bridging the Gap Between Clinical Benefits, Access and Equipment Utilization," SignaPULSE—A GE Healthcare MR Publication, Spring 2009, 5 pages.
Update of AAPM Task Group No. 43 Report: A revised AAPM protocol for brachytherapy does calculations; Med. Phys. vol. 31 No. 3, Mar. 2004; pp. 633-674.
Supplement to the 2004 update of the AAPM Task Group No. 43 Report; Med. Phys. vol. 34 No. 6, Jun. 2007; pp. 2187-2206.
Erratum: "Update of AAPM Task Group No. 43 Report: A revised AAPM protocol for brachytherapy dose calculations" [Med. Phys. 31, 633-674 (2004)].
Pagoulatos et al., "Interactive 3-D Registration of Ultrasound and Magnetic Resonance Images Based on a Magnetic Position Sensor," IEEE Transactions on Information Technology in Biomedicine, vol. 3, No. 4, Dec. 1999, 11 pages.

* cited by examiner

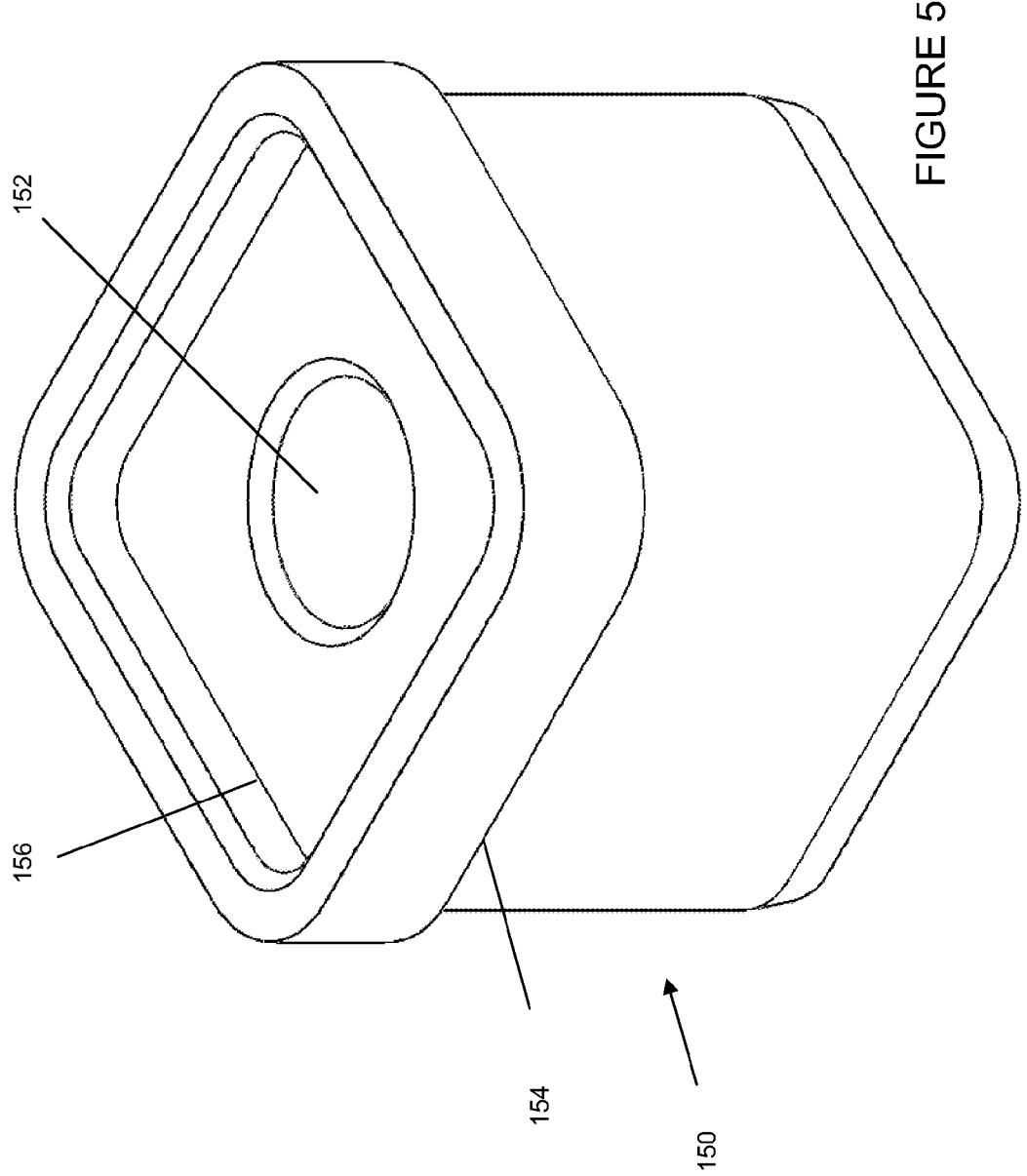

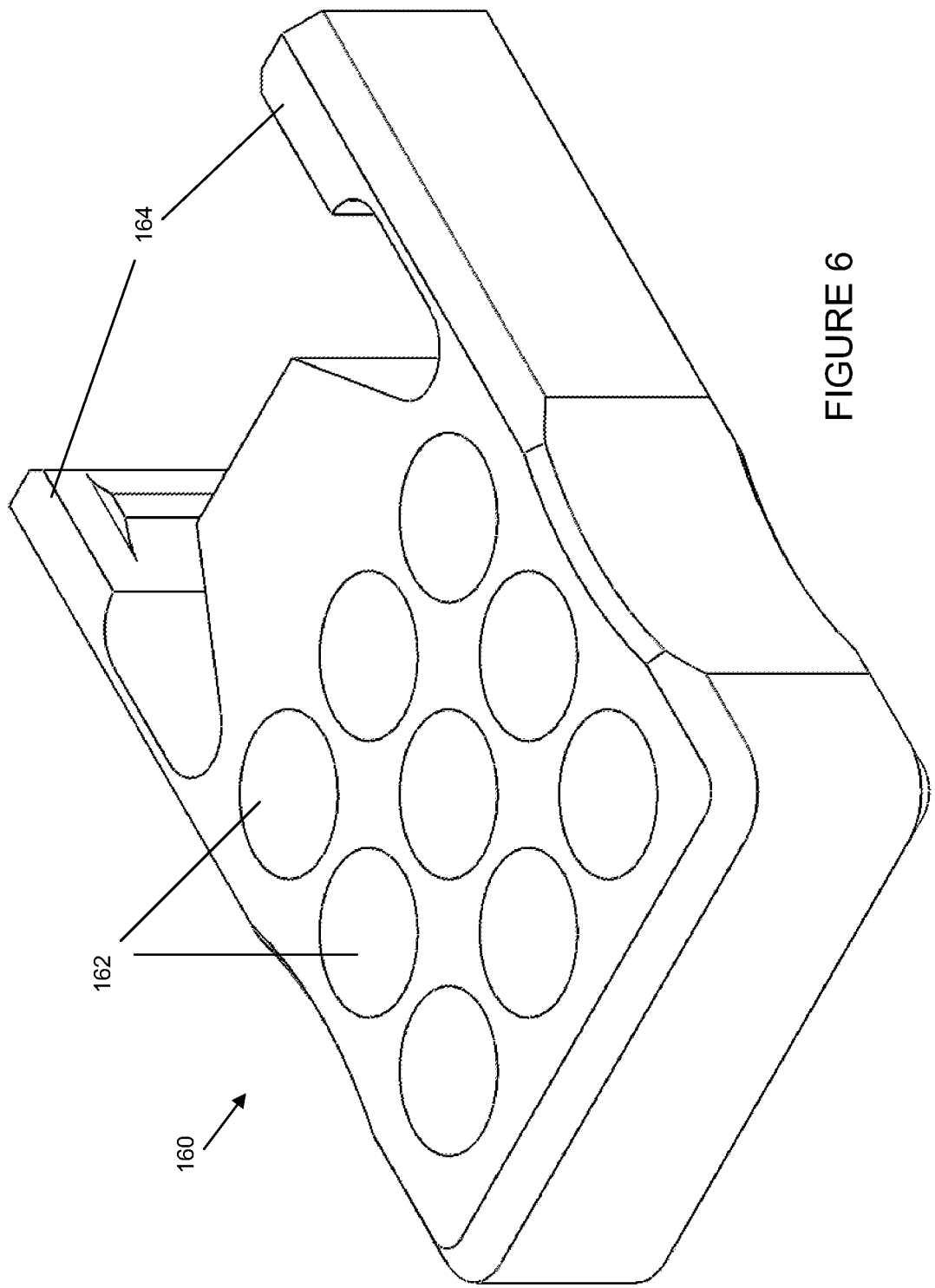

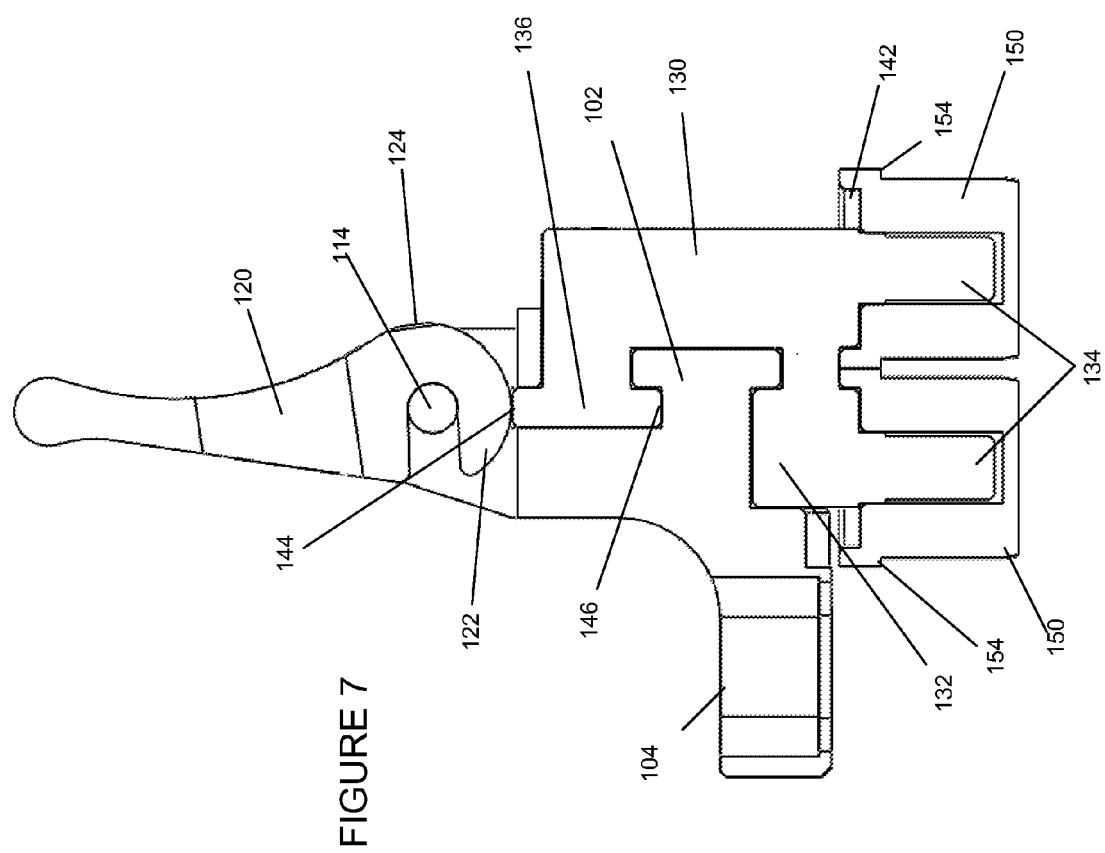

VARIABLE ANGLE GUIDE HOLDER FOR A BIOPSY GUIDE PLUG

RELATED APPLICATIONS

This application claims priority from U.S. Provisional Application 61/213,594 filed Jun. 23, 2009, the contents of which are herein incorporated by reference.

FIELD OF INVENTION

This invention relates to a guidance apparatus and methods for guiding interventional devices into tissue.

BACKGROUND

In medical or health procedures, use of guides improves the accuracy of instrument placement into tissue. In addition, imaging systems provide visual guidance based on measurements from various imaging formats. These imaging formats (such as Magnetic Resonance Imaging (MRI), sonographs (ultrasound), fluoroscopy, X-ray, and the like) can locate an interventional device in relation to treatment or therapy-targeted tissue, such as MRI-detected target tissue. These imaging formats can generate imaging data that may be used to determine the appropriate positing of the interventional device or instrument.

As an example, MRI may be used to detect faint nuclear magnetic resonance (NMR) signals limited by protons in the presence of a string magnetic field after excitation by a radio frequency signal, such as by way of antenna(e) termed "coils". The detected signal can then be analyzed to produce an image of the internal structure of tissue within the patient being imaged.

For purposes of example, when attempting to examine breast tissue, the tissue of interest may be compressed or held in position between two immobilization plates, which may hold the breast in a medial-lateral direction such that it is immobilized during acquisition of an MRI image. These immobilization plates may further consist of a number of apertures, and with a plurality of apertures such that a grid, or other co-ordinate positioning system, can be formed. These apertures may also allow interventional devices to pass through the immobilization plate to access the tissue. Immobilization plates having a large number of apertures in a grid pattern sized to support and guide interventional devices, can tend to be cumbersome as, for example, a new plate may be required for interventional devices having different diameters. This may require the use of a different immobilization plate for each intervention guide being used. This also may prevent the ability to use interventional devices of different diameters without multiple scans. Furthermore, this may cause shifting in the tissue being immobilized when plates are being exchanged or moved. Immobilization plates, therefore, may alternatively have apertures larger than the interventional devices, into which an adaptor, guide, block or plug may be inserted. These can be generically referred to as guide plugs, which may have one or several holes for assisting in positioning an interventional device to a target. The guidance may be provided by, for example, a grid of holes, which may be perpendicular to the immobilization plate, through the plug. Alternatively a plug may be provided with a non-grid pattern of holes, perpendicular to the immobilization plate, in various parts of the plug where the plug may be movable to multiple positions, for example by removing the plug and re-inserting the plug into the immobilization plate in a different orientation, to align one of the holes as close as possible with the target region of the tissue. As a consequence, the positioning capability of any interventional device is limited.

SUMMARY OF THE INVENTION

In an aspect of the present invention, there is provided a variable angle guide plug holder for use in interventional procedures comprising: a guide plug holder for receiving an angular determination fixture; the guide plug holder movable relative to the angular determination fixture between a plurality of positions, each position providing a different angle of insertion relative to a point of origin on the angular determination fixture; and plate plug engaged with the angular determination fixture wherein the plate plug is insertable into a guide plate aperture of a guide plate for use in an interventional procedure. The angle of insertion can be selected by a user and such angle of insertion may be between a first angle of insertion and a second angle of insertion.

The variable angle guide plug holder can further comprise a locking arm connected to the guide plug holder. The locking arm can be movable between a locked and an unlocked position and can be removeably engageable with the angular determination fixture when positioned in the locked position which can tend to prevent movement of the guide plug holder relative to the angular determination fixture.

The guide plug holder of the variable angle guide plug holder can further comprise fiducial holder receptacles for receiving a fiducial holder. The fiducial holder may be able to receive a fiducial for verifying the angle of insertion during an image guided interventional procedure.

The guide plug holder of the variable angled plug holder can be movable in an arched path relative to the angular determination fixture. The guide plug holder may be movable to an angle of insertion which may be between 89 degrees and −89 degrees, relative to the point of origin, and in other embodiments, the angle of insertion may be between 30 and −30 degrees.

In another aspect of the present invention, there is provided a variable angle guide plug holder for use in interventional procedures, comprising: a guide plug holder having a groove for receiving a track connected to an angular determination fixture; the track slideable within the groove for moving the guide plug holder relative to the angular determination fixture in an arched path between a plurality of positions, each position providing a different angle of insertion relative to a point of origin on the angular determination fixture; a locking arm connected to the guide plug holder, the locking arm movable between a locked and an unlocked position and removeably engageable with an upper surface of the track when positioned in the locked position to prevent movement of the guide plug holder relative to the angular determination fixture; and plate plug engaged with the angular determination fixture wherein the plate plug is insertable into a guide plate aperture of a guide plate for use in an interventional procedure.

In another aspect of the present invention, there is provided a method of configuring a variable angle guide plug holder for the purpose of conducting an interventional procedure, comprising the steps of: determining an angle for insertion of a medical instrument for relative to a point of origin; inserting the variable angle guide plug holder into a guide plate aperture of a guide plate; setting the variable angle guide plug holder having guide plug holder to the determined angle; inserting a guide plug into a guide plug holder; and inserting a medical instrument through the guide plug to a tissue of interest.

The method can further comprise the steps of: connecting a fiducial holder to the guide plug holder; inserting a fiducial through a fiducial aperture of the fiducial holder; imaging a patient using an imaging system to obtain an image displaying the tissue of interest and the fiducial; verifying the angle of insertion based on the image; and removing the fiducial holder from the guide plug holder.

In other aspects, methods and apparatus relating to the systems described above are also provided.

BRIEF DESCRIPTION OF DRAWINGS

For a better understanding of embodiments of the system and methods described herein, and to show more clearly how they may be carried into effect, reference will be made by way of example, to the accompanying drawings in which:

FIG. 5 shows an isometric view of an embodiment of a plate plug;

FIG. 6 shows an isometric view of an embodiment of a fiducial holder;

FIG. 7 shows a cross-section of the variable angled guide plug holder of FIG. 1 cut along the line 7-7;

Figure 1:
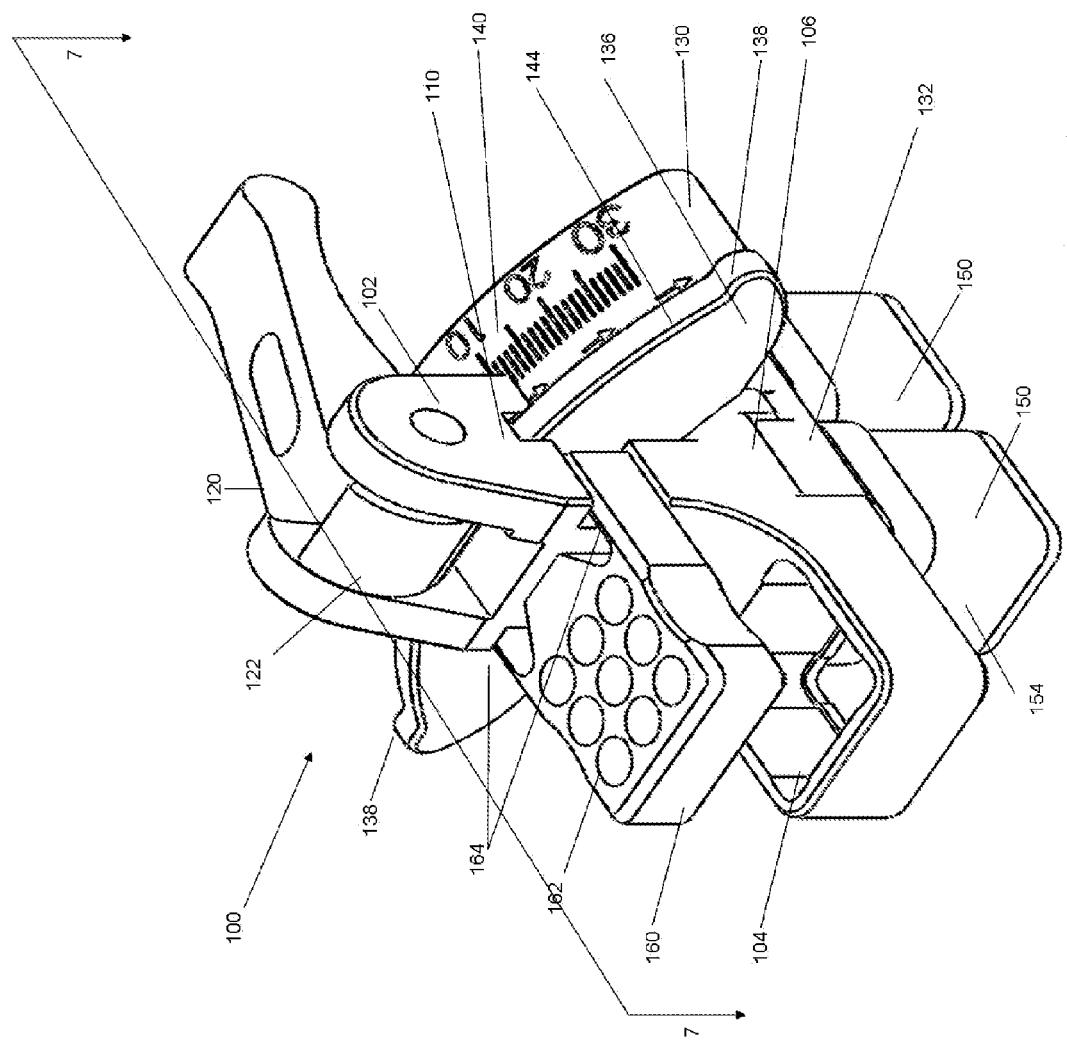
FIG. 1 shows an isometric view of an embodiment of a variable angled guide plug holder.

It will be appreciated that for simplicity and clarity of illustration, elements shown in the figures have not necessarily been drawn to scale. For example, the dimensions of some of the elements may be exaggerated relative to other elements for clarity.

DESCRIPTION

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

With reference to FIG. 1, an embodiment of variable angled guide plug holder 100 for use in an interventional procedure, such as a biopsy, on a tissue of interest in a patient, is shown. Variable angled guide plug holder 100 comprises guide plug holder 102, locking arm 120, angular determination fixture 130, and plate plugs 150. Guide plug holder 102 can be slideably connected to angular determination fixture 130 along track 136 received by a groove which can be formed by upper track groove 110 and bottom track groove 108 such that guide plug holder 102 can slide in an arched path relative to angular determination fixture 130.

Glide plug holder 102 may be removable from angular determination fixture 130, and in some embodiments, may slide off track 136. When locking arm 120 is engaged with guide plug holder 102, locking arm 120 prevents guide plug holder 102 from disengaging from angular determination fixture 130. In such embodiments track 136 may have track stops 138 which may be located at positions along track 136, such as, for example, at the end positions of track 136 and as guide plug holder 102 is slid on track 136, track stops 138 may engage a locking portion of locking arm, preventing further sliding of guide plug holder 102 along track 136 in one direction.

Plate plugs 150 can be removably connected to angular determination fixture 130, such plate plugs 150 for engagement with guide plate aperture 192 of guide plate 190 (shown in FIGS. 9-12). Guide plate 190 can be used in an interventional procedure, and can be used in an image guided interventional procedure, such as an MRI image guided procedure. Plate plugs 150 may be inserted into guide plate aperture 192 which may tend to position variable angled guide plug holder 100 in a position relative to a tissue of interest useful for performing an interventional procedure on a tissue of interest in a patient, such as a biopsy. Plate plugs 150 may have stop ridge 154 which may tend to engage an outer surface of guide plate 192 to prevent plate plugs 150 from sliding through plate plug aperture 192. Plate plug 150, when inserted into guide plate aperture 192, may prevent movement of angular determination fixture 130 relative to guide plate 190.

Figure 11:
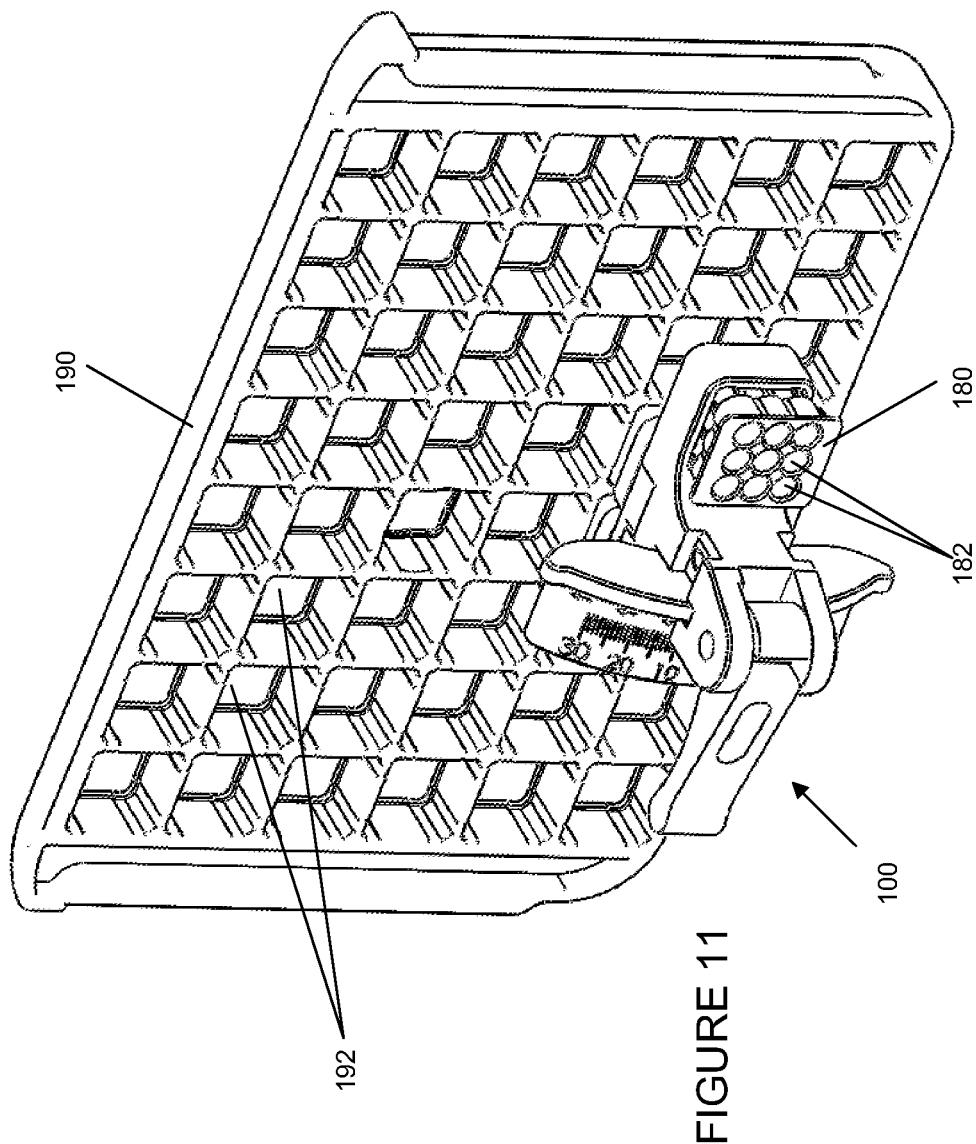
FIG. 11 shows an isometric view of the variable angled guide plug holder of FIG. 1 with the fiducial holder disengaged and the guide plug securing mechanism engaged with a guide plug.
Figure 12:
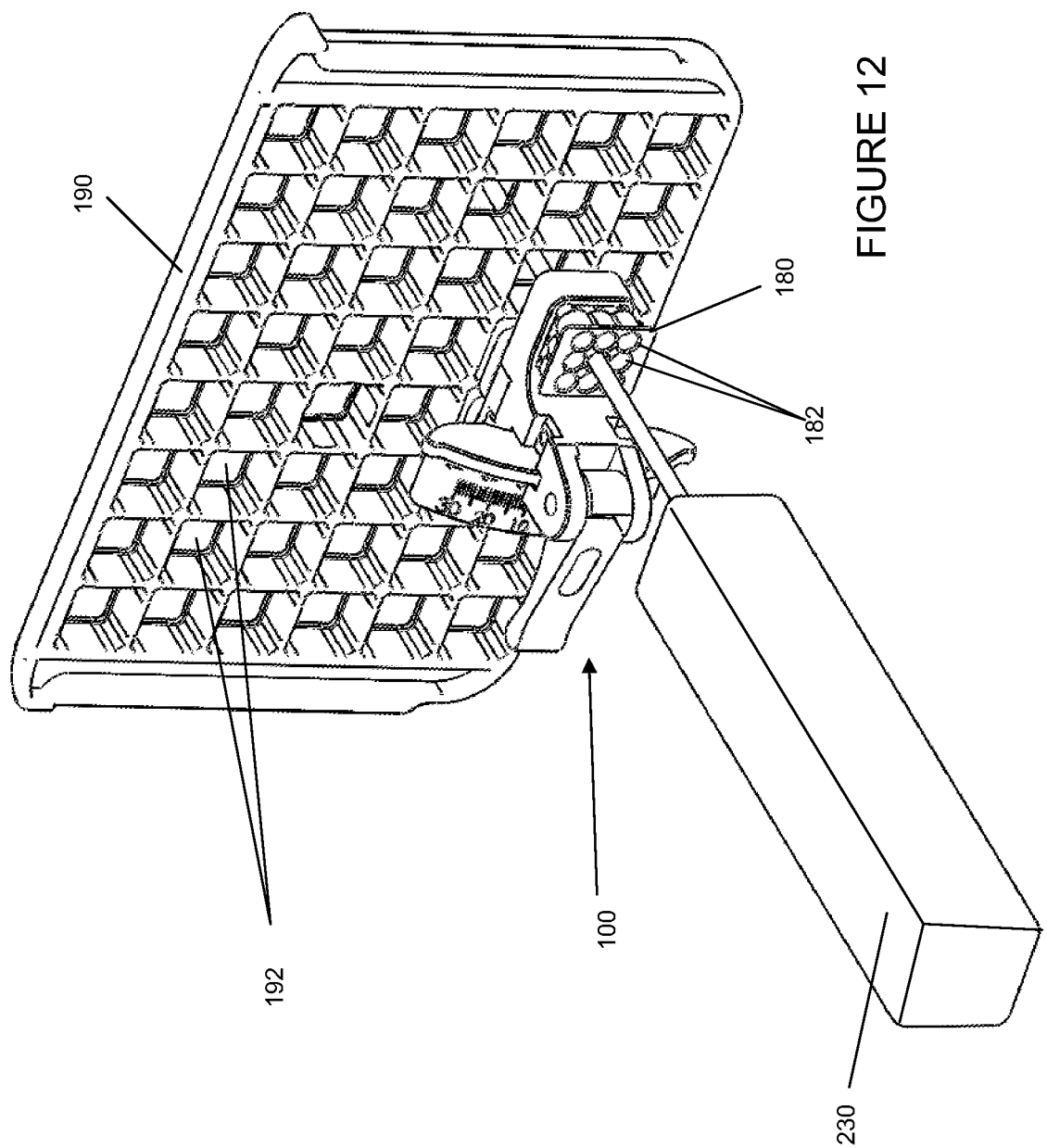
FIG. 12 shows an isometric view of the variable angled guide plug holder of FIG. 11 with a medical instrument inserted into the guide plug.

Variable angled guide plug holder 100 can receive guide plug 180 (as shown in FIG. 11) in guide plug securing mechanism 104, guide plug 180 for receiving a medical instrument 230 in guide aperture 182, which may be used in an interventional procedure on a tissue of interest in a patient, such as a biopsy.

Figure 8:
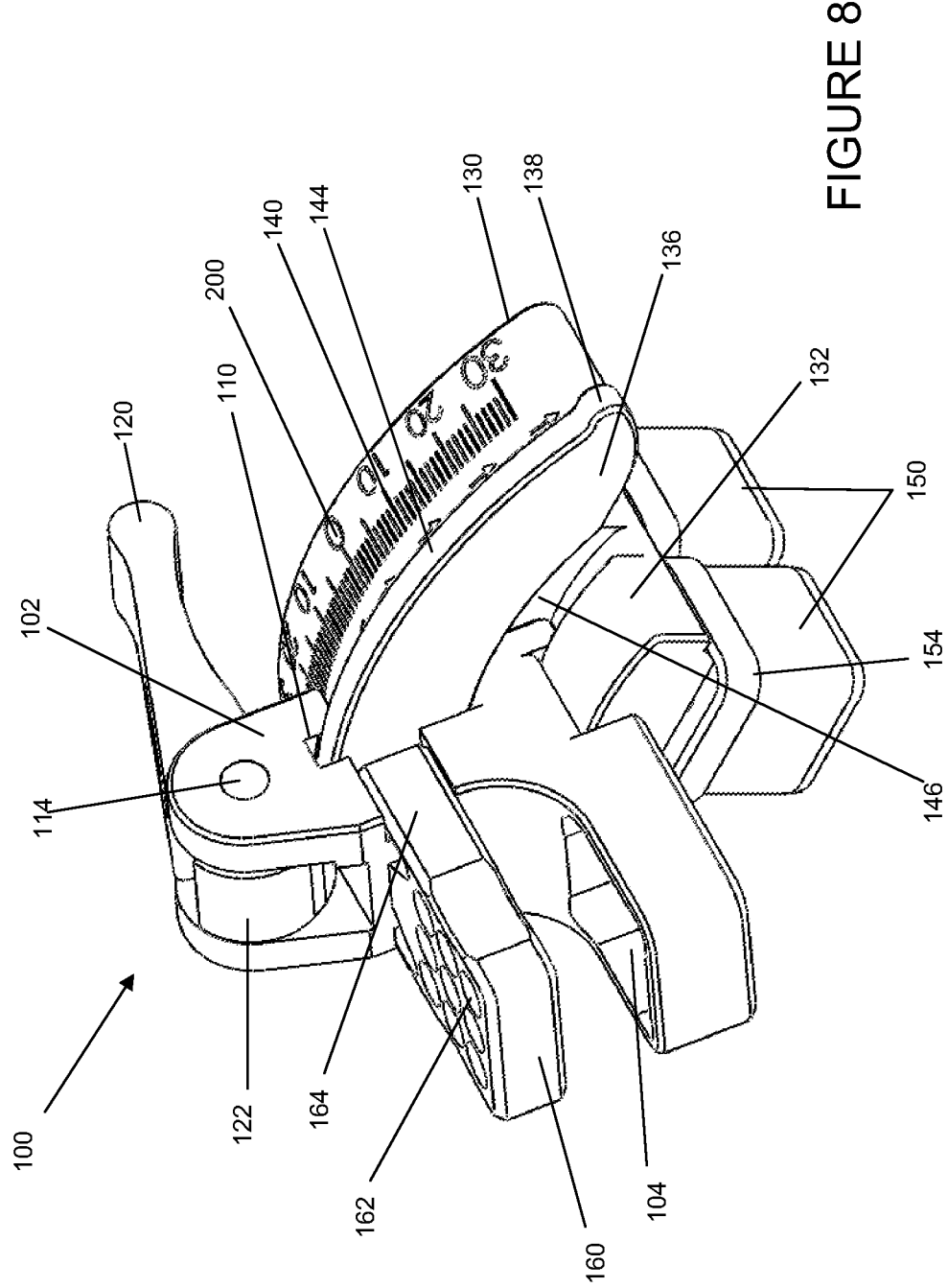
FIG. 8 shows an isometric view of the variable angled guide plug holder of FIG. 1 at an angle of insertion of 30 degrees and in the locked position.

The arched path tends to allow a user to position guide plug holder 102 in a variety of angled positions when slid along arched path relative to angular determination fixture 130. When plate plugs 150 are inserted into guide plate aperture 192, user may adjust the angle of guide plug holder 102 relative to angular determination fixture to select a desired angle of guide plug holder 102 relative to angular determination fixture 130 that may be useful in an interventional procedure on a tissue of interest in a patient, such as a biopsy. In some embodiments, the arched path may allow a user to position guide plug holder 102 in a variety of angled positions ranging between 89 degrees and −89 degrees relative to point of origin 200. In other embodiments, the variety of angled positions may range between 30 and −30 degrees relative to a point of origin (as shown in FIG. 8) which represents an example of the effective angular range needles of various gauges.

Locking arm 120 can be removably connected to guide plug holder 102 and may be moved between a locked and an unlocked positions. Guide plug holder 102 can be prevented from sliding in an arched path relative to angular determination fixture 130 when locking arm 120 is in a locked position and can be movable along the arched path when locking arm 120 is in the unlocked position.

Figure 10:
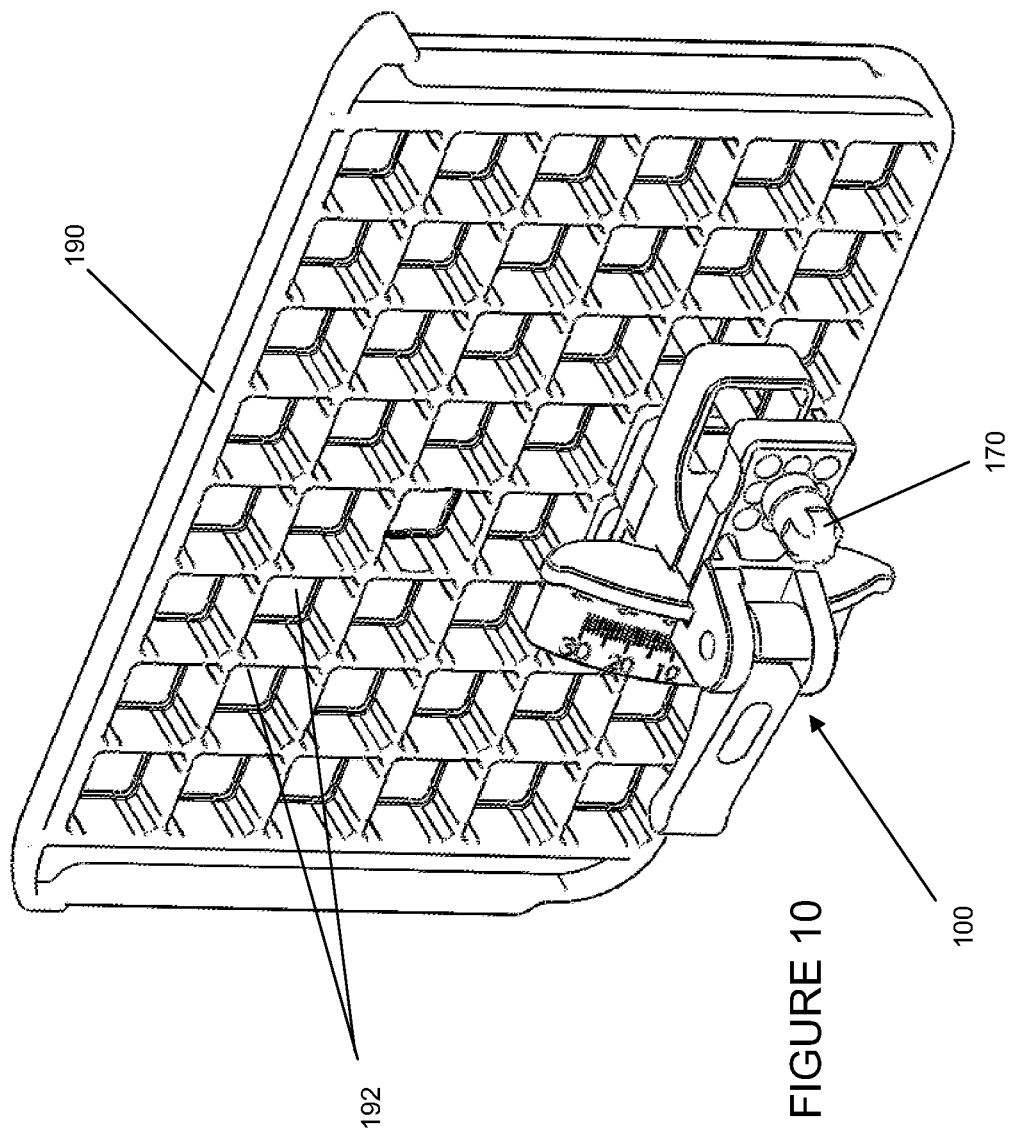
FIG. 10 shows an isometric view of the variable angled guide plug holder of FIG. 9 a fiducial inserted into the fiducial holder.

Variable angled guide plug holder 100 may optionally have removable fiducial holder 160 which may have fiducial holder engagement mechanism 164 for removable engagement with fiducial holder receptacles 162. Fiducial holder 160 may have fiducial receiving apertures, for receiving fiducial 170 (as shown in FIG. 10). Fiducial holder 160 may be useful prior to an interventional procedure, such as a biopsy, to verify, using imaging techniques, that the desired angle of guide plug holder 102 relative to angular determination fixture 130 is aligned with the tissue of interest. For example, angled biopsy guide holder 100 may be positioned within guide plate 190 which may be positioned close to a tissue of interest. A desired angled of guide plug holder 102 relative to angular determination fixture 130 may be selected and fiducial holder 160 may be engaged with guide plug holder 102 and fiducial 170 may be inserted in fiducial holder receptacles 162. The tissue of interest may be imaged using an appropriate imaging technique, for example MRI imaging, and the resulting image may tend to show the path of fiducial 160 relative to the tissue of interest, which may tend to provide a user with an image that may verify that guide plug holder 102 is in a position relative to angular determination fixture 130 such that when fiducial holder 160 is removed, guide plug 180 may be engaged in plug securing mechanism 104 for insertion of a medical instrument 230 in guide aperture 182, such that a medical instrument 230 may engage a tissue of interest in a patient during an interventional procedure, such as a biopsy.

Figure 2A:
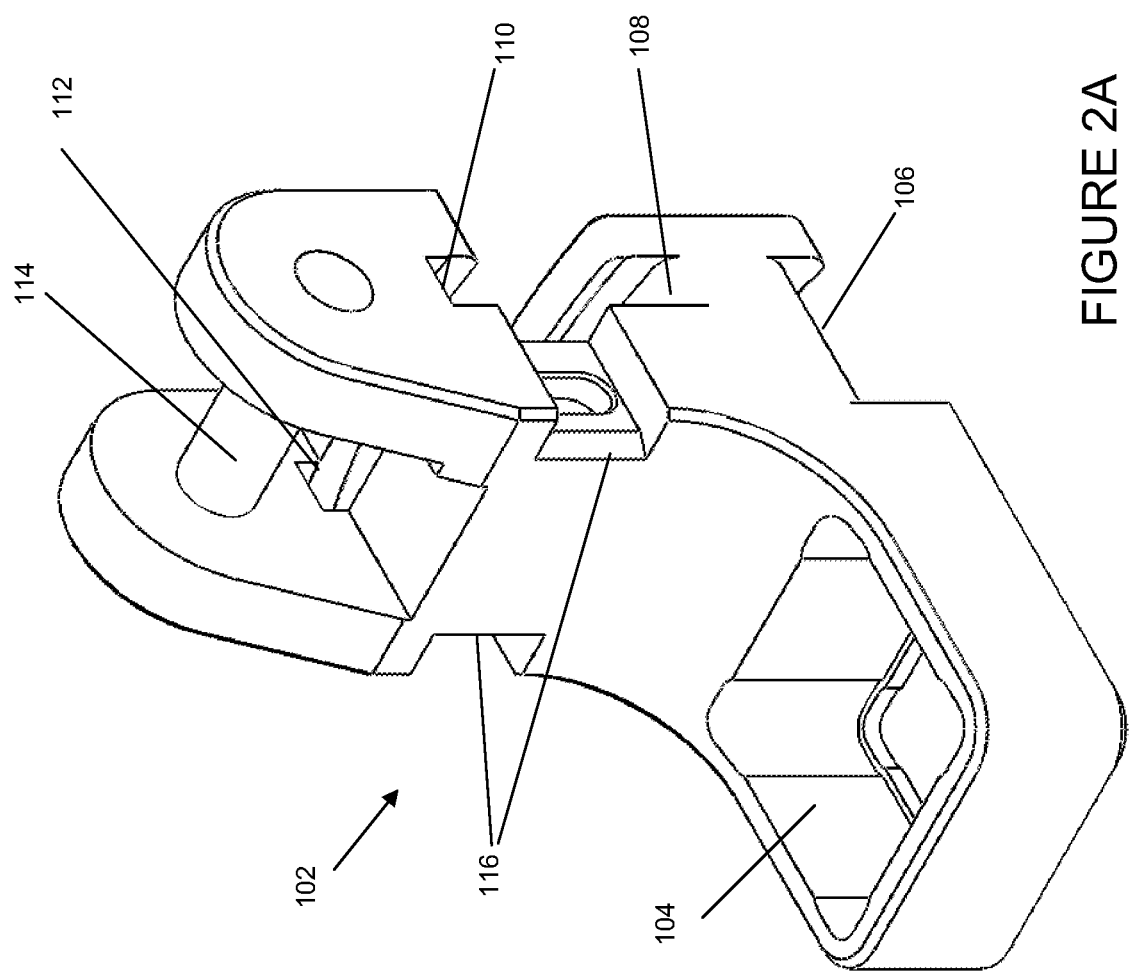
FIGS. 2A and 2B show isometric views of an embodiment of a guide plug holder.
Figure 2B:
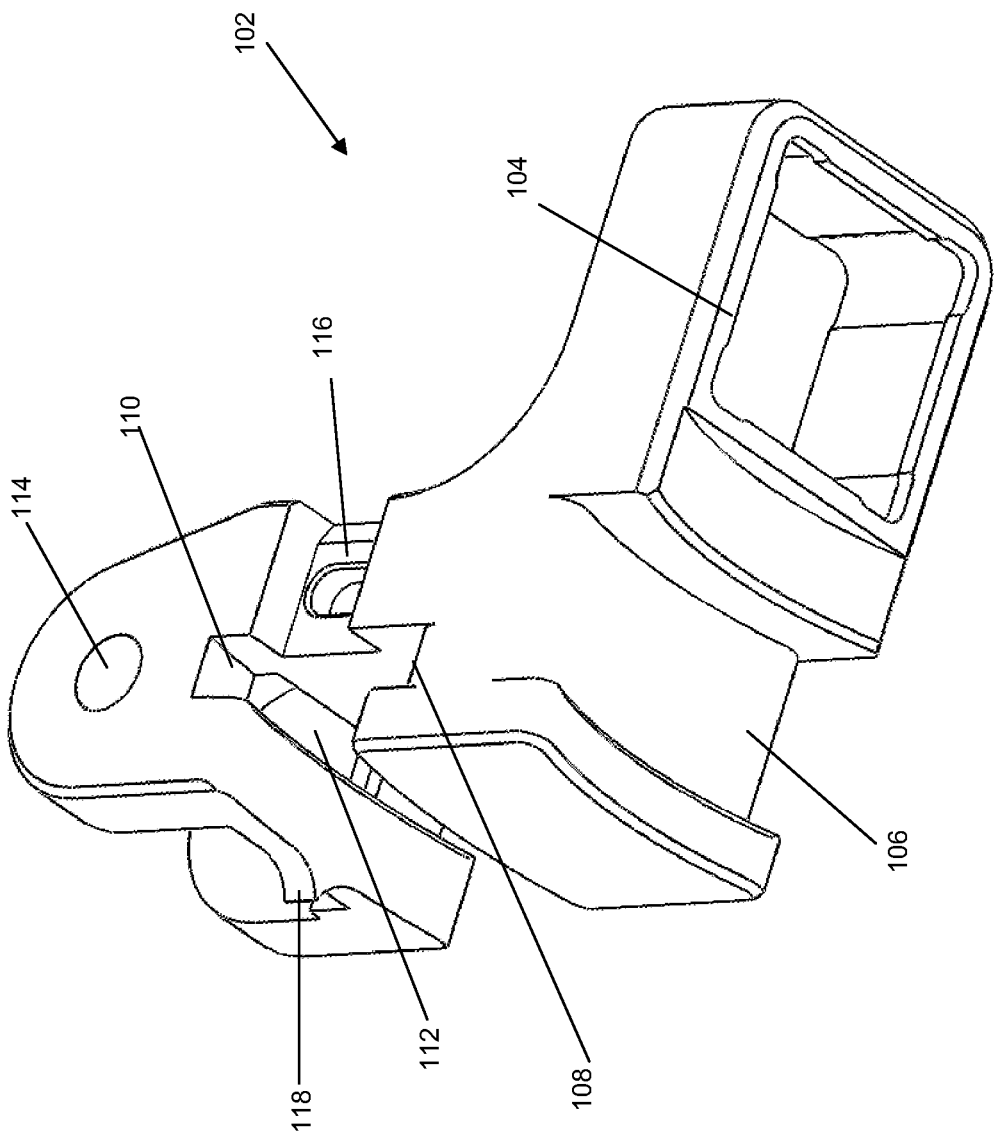
Figure 9:
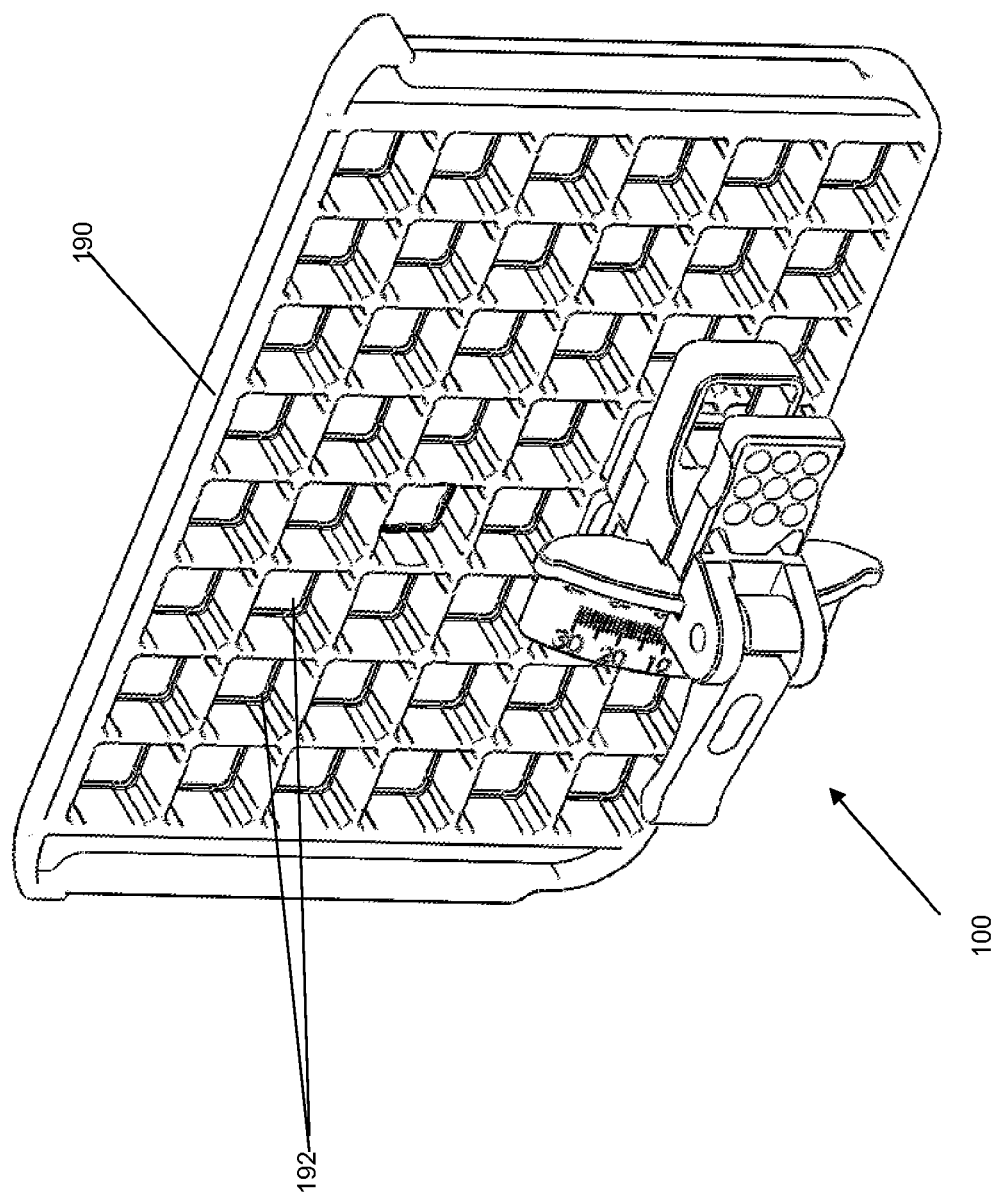
FIG. 9 shows an isometric view of the variable angled guide plug holder of FIG. 1 inserted into a guide plate.

With reference to FIGS. 2A and B, an embodiment of guide plug holder 102 is shown. Guide plug holder 102 has plug securing mechanism 104 for receiving guide plug 180 (as seen in FIG. 9). Guide plug holder 102 may secure guide plug 180 in plug securing mechanism 104 by a frictional engagement and, in some embodiments, plug securing mechanism 104 may have inward protruding ridge which may tend to prevent guide plug 180 from traveling through plug securing mechanism 104 upon insertion of guide plug 180 into plug securing mechanism 104.

Guide plug holder 102 may have lower slide groove 106 for slideable engagement with corresponding lower slide protrusion 132. Lower slide groove 106 and lower slide protrusion 132 may be arched shaped. When lower slide groove 106 is engaged with lower slide protrusion 132 and arched shaped outer surface of lower slide groove 106 contacts a corresponding arched shaped outer surface of lower slide protrusion 132, such that when lower slide protrusion 132 slides within lower slide groove 106 the direction of slide is arched shaped. Such slideable engagement can tend to allow guide plug holder 102 to be slid between various angled positions when in use. When guide plug holder 102 is engaged with angular determination fixture 130, lower slide protrusion 132 can be positioned within corresponding lower slide groove 106 and can prevent movement of guide plug holder 102 relative to angular determination fixture 130 except in the arched direction that lower slide protrusion 132 may be slid within lower slide groove 106, thus providing appropriate mechanical support during the insertion and subsequent retraction of any interventional device.

Guide plug holder can have a groove comprising bottom track groove 108 and upper track groove 110. Bottom track groove 108 can provide slideable engagement with corresponding bottom track surface 146 of track 136. Bottom track groove 108 and bottom track surface 146 may be arched shaped such that when bottom track groove 108 is engaged with bottom track surface 146 an arched shaped outer surface of bottom track groove 108 contacts a corresponding arched shaped outer surface of bottom track surface 146, such that when bottom track surface 146 slides within bottom track groove 108 the direction of slide is arched shaped. Such slideable engagement can tend to allow guide plug holder 102 to be slid between various angled positions when in use. When guide plug holder 102 is engaged with angular determination fixture 130, bottom track surface 146 can be positioned within corresponding bottom track groove 108 and can tend to prevent movement of guide plug holder 102 relative to angular determination fixture 130 except in the arched direction that bottom track surface 146 may be slid within bottom track groove 108, such slideable arched direction tending to be the same as the slideable direction that lower slide protrusion 132 may be slid within lower slide groove 106.

Figure 3A:
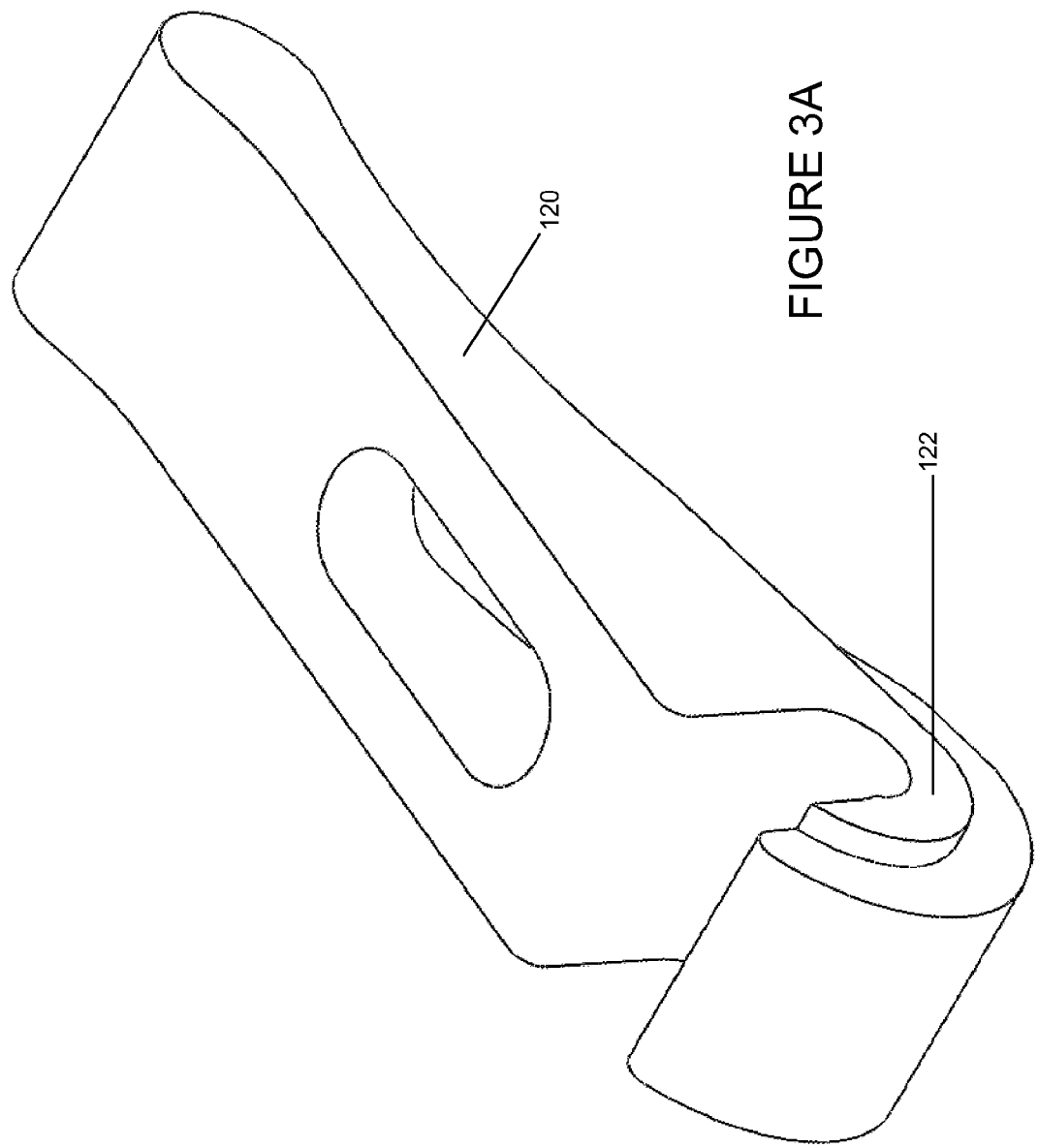
FIGS. 3A and 3B show isometric views of an embodiment of a locking arm.
Figure 3B:
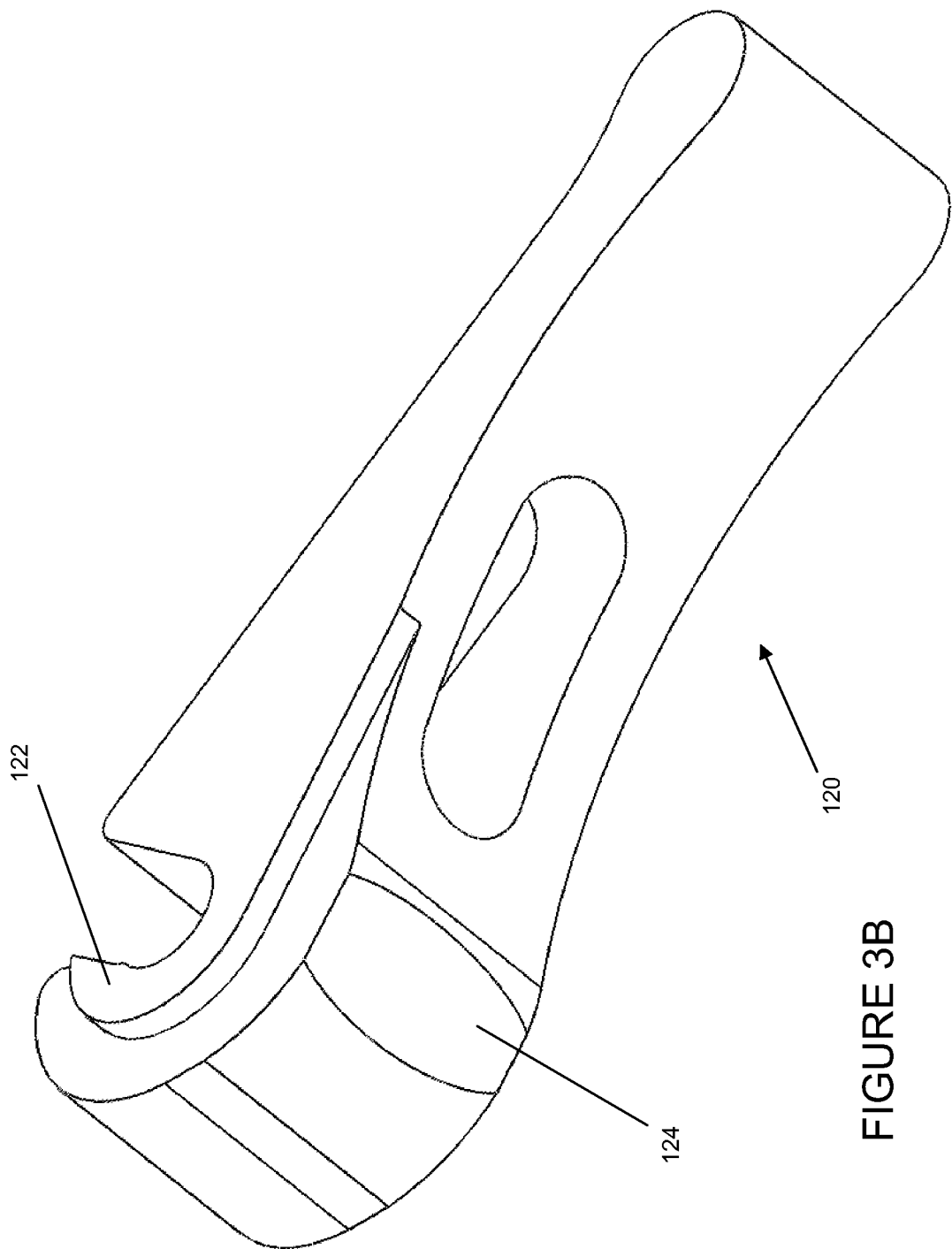

Guide plug holder 102 may have pin 114 for engagement with locking arm 120. With additional reference to FIGS. 3A and B, locking arm 120 may have locking mechanism 122 which may engage with pin and may tend to allow rotational movement of locking arm 120 relative to guide plug holder 102. Locking arm 120 may rotate about pin 114 relative to guide plug holder 102 between a locked position and an unlocked position, when in the locked position, locking engagement surface 124 may frictionally engage with upper track surface 144 of guide plug holder 102 through opening 112, which may tend to prevent movement of guide plug holder 102 relative to angular determination fixture 130 until locking arm 120 is placed in an unlocked position.

Guide plug holder 102 may have upper track groove 110 for receiving corresponding upper track surface 144 of track 136, upper track slot may have opening 112 which can tend to provide access to upper track surface 114 for locking arm 120, which can tend to allow locking engagement surface 124 to frictionally engage upper track when locking arm 120 is in the locked position. Upper track surface 144 may be arched shaped. Upper track groove 110 may be slideably received by upper track groove 110 as guide plug holder 102 slides in an arched direction relative to angular determination fixture 130, as may be provided by bottom track surface 146 sliding within bottom track groove 108 and lower slide protrusion 132 sliding within lower slide groove 106.

Guide plug holder 102 may have fiducial holder receptacles 116 for removable engagement with fiducial holder 160. With additional reference to FIG. 6, fiducial holder 160 may have fiducial holder engagement arms 164 which may form a lock with fiducial holder receptacles 116.

Guide plug holder 102 may have angle position marker 118 which, with additional reference to FIG. 4, may be in alignment with angle markers 140 such that angle position marker 118 may tend to indicate to a user of variable angled guide plug holder 100 the angled position of guide plug holder 102 relative to angular determination fixture 130.

Figure 4A:
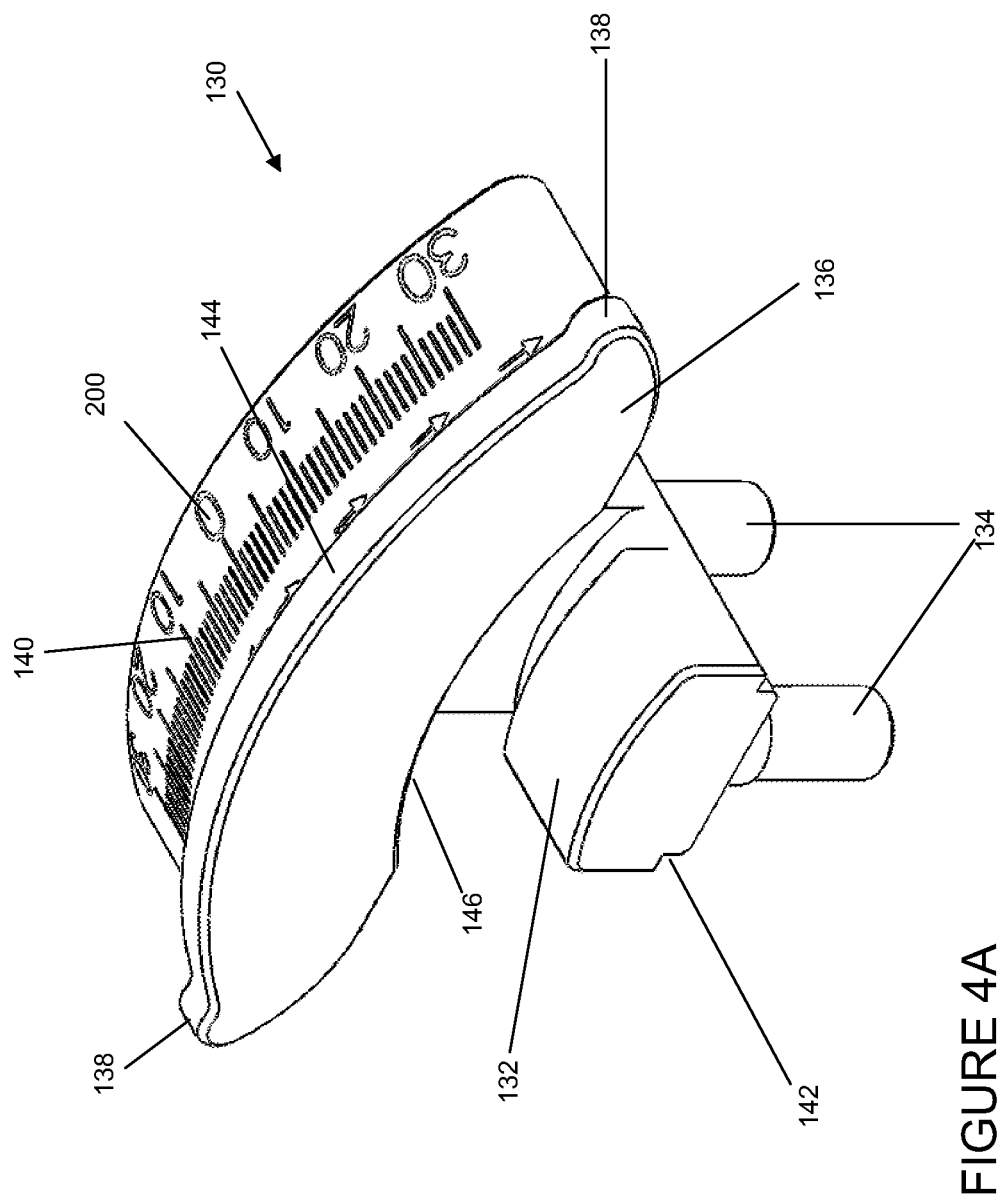
FIGS. 4A and 4B show isometric views of an embodiment of an angular determination fixture.
Figure 4B:
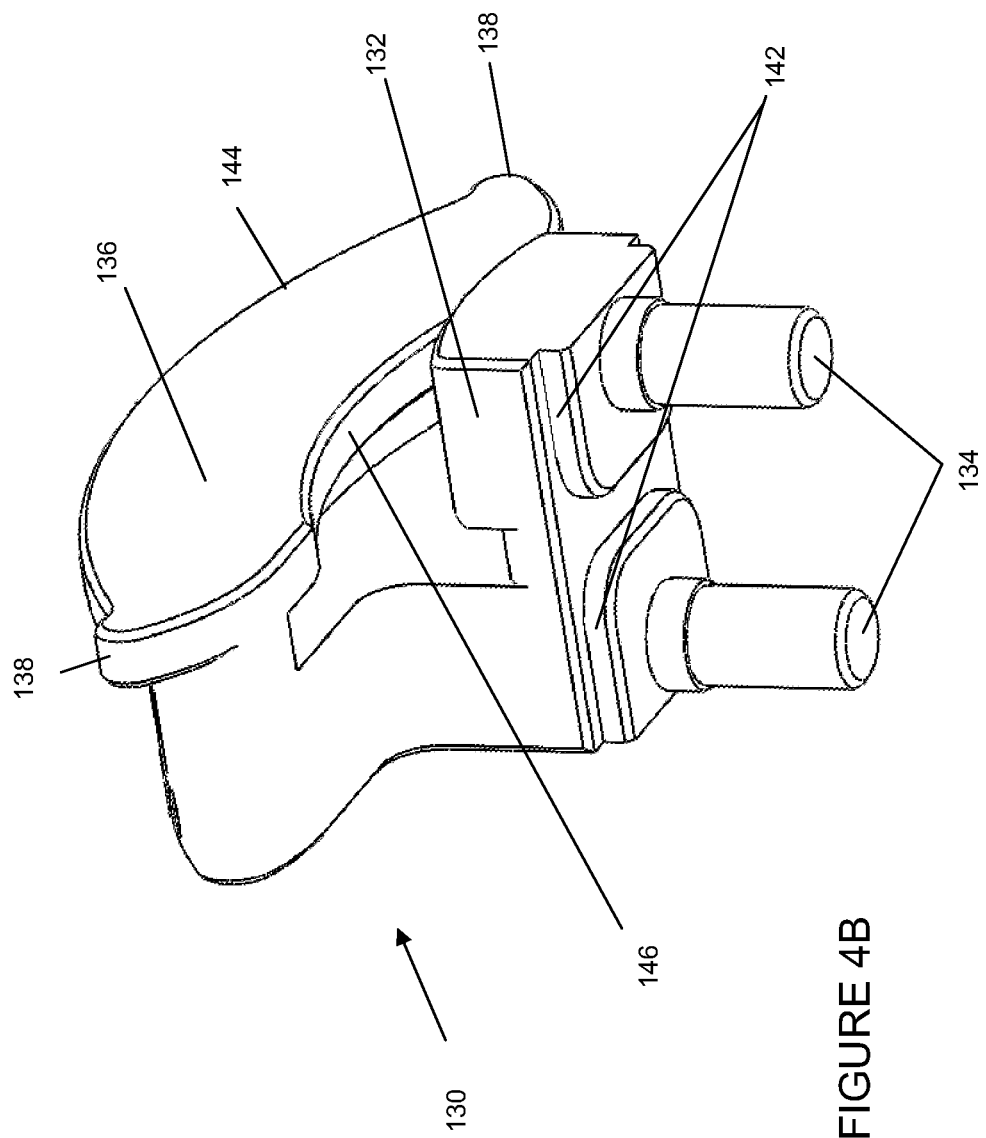

With reference to FIGS. 4A and 4B, angular determination fixture 130 may have lower slide protrusion 132 which, as described above, may slideably engage with lower slide grove 106. Angular determination fixture 130 may have track 136 having upper track surface 114 and bottom track surface 146 which, as described above, may slideably engage with upper track grove 110 and bottom track groove 108 respectively. Angular determination fixture 130 may have angle markers 140 which, as described above, may be in alignment with angle position marker 118 and may tend to indicate to a user of variable angled guide plug holder 100 the angled position of guide plug holder 102 relative to angular determination fixture 130. In some embodiments, point of origin 200 may be marked by 0 degrees and the angles between which guide plug holder 102 may be positioned relative to angular determination fixture 130 can be 30 degrees in one direction and 30 degrees in the other direction from point of origin 200.

Angular determination fixture 130 may have plug engagement post 134 for removable connection with plate plugs 150 (see FIG. 5). Plug engagement post 134 can engage with corresponding post receiving aperture 152 in plate plugs 150. Alignment ridge 142 on angular determination fixture 130 may removeably engage with corresponding alignment groove 156, may tend to form a frictional engagement and may tend to align plate plugs 150 relative to angular determination fixture 130. Alignment ridge 142 when engaged with corresponding alignment groove 156 may additionally tend to prevent rotational movement of plate plugs 150 relative angular determination fixture 130. In some embodiments, angular determination fixture 130 may have multiple plate engagement posts 134 for engagement with multiple plate plugs 150.

Track 136 may have track stops 138 which may protrude from upper track surface 144. Track stops 138 at predetermined positions and, in some embodiments, may be positioned at opposite ends of track 136. Track stops 138 may prevent guide plug holder 102, when guide plug holder 102 is slideably engaged to angular determination fixture 130, from sliding beyond a predetermined position. With additional reference to FIG. 7, when guide plug holder 102 is slideably engaged to angular determination fixture 130, locking arm 120 is engaged with pin 114 and locking arm 120 is in an unlocked position, track stops 138 may slide through upper track groove 110 and may engage with lock mechanism 124, such engagement tending to prevent additional slideable movement of guide plug holder 102 relative to angular determination fixture 130. In some embodiments, when locking arm 120 is disengaged with pin 114, track stops 138 may be slideable through upper track groove 110 such that guide plug holder 102 may be disengageable from angular determination fixture 130 by sliding guide plug holder 102 off angular determination fixture 130.

With reference to FIG. 9, in use, variable angled guide plug holder 100 may be in an interventional procedure, and in some embodiments, in an image guided interventional procedure, for example a biopsy. In an embodiment involving a breast biopsy, a patient may be positioned in a prone position, on a patient support system, wherein the MRI scanning table may provide a large interventional access area whereby the patient's breasts may fall into an opening at the chest level of the MRI scanning table and can then be immobilized by a guide plates 190, for example, in the medial-lateral direction access area. The patient's breast may then be compressed between guide plates 190 which may tend to maintain the shape of the patient's breast and to immobilize the position of the patient's breast. Guide plates 190 may have guide plate apertures 192 for receiving variable angled guide plug holder 100.

Figure 13:
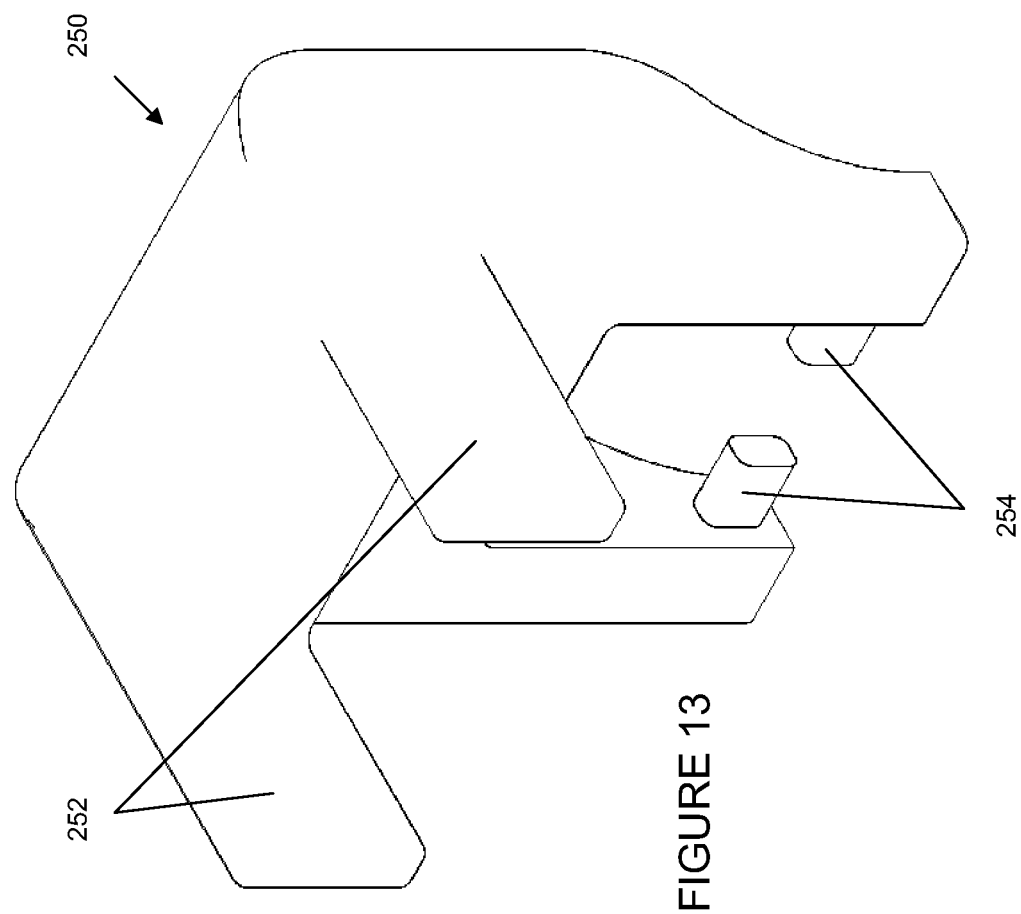
FIG. 13 shows an isometric view of an embodiment of a medical instrument support attachment.
Figure 14A:
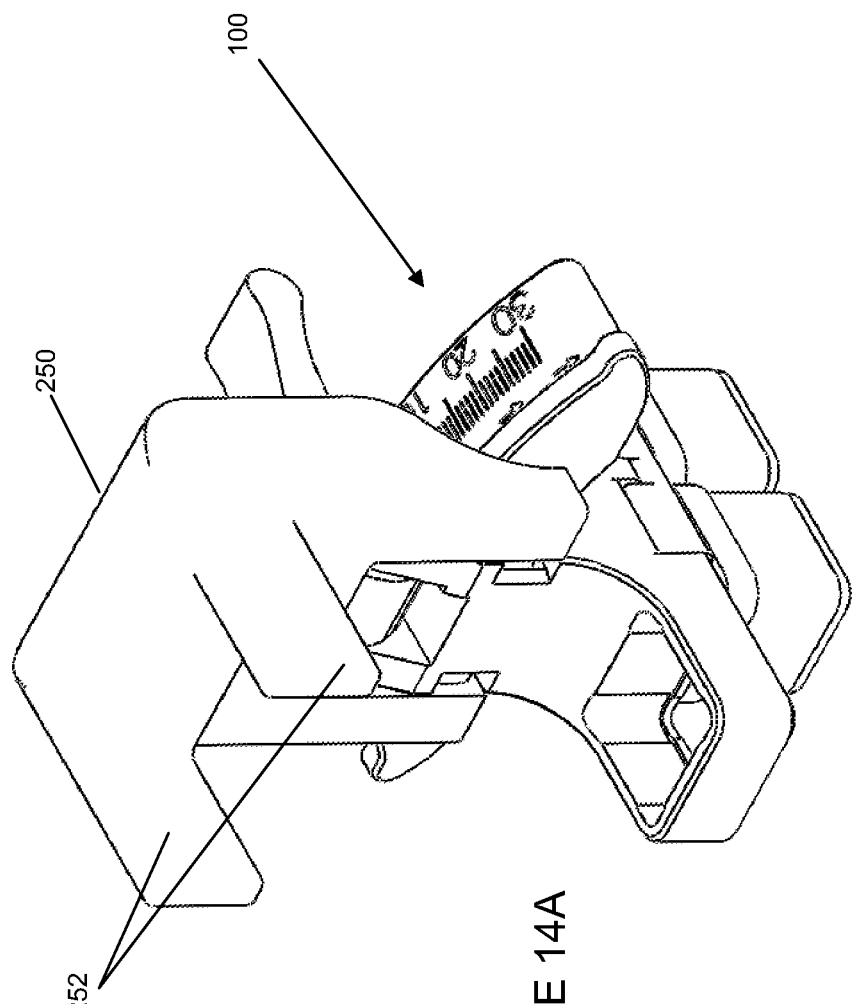
FIG. 14A shows the medical instrument support attachment of FIG. 13 engaged with the variable angled guide plug holder of FIG. 1.
Figure 14B:
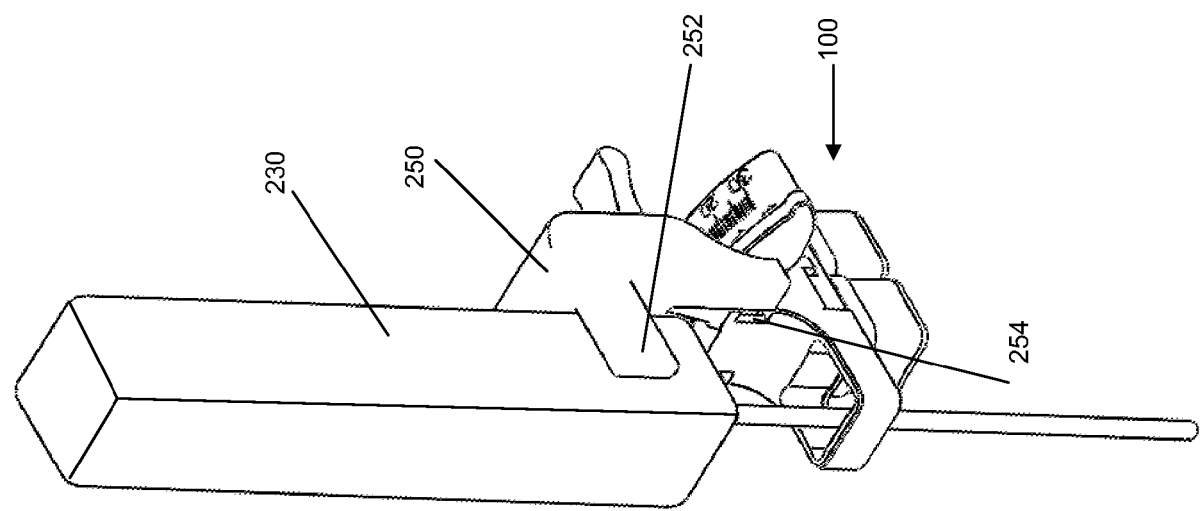
FIG. 14B shows the medical instrument support attachment of FIG. 13 engaged with a medical instrument.

With reference to FIGS. 14A and B, medical instrument support attachment 250 may connected to variable angled guide plug holder 100 and may tend to provide support to medical instrument 230 during an interventional procedure. With additional reference to FIG. 13, medical instrument support attachment 250 may comprise medical instrument supports 252 which may tend to provide support for medical instrument 230 and, in some embodiments, may slideably engage medical instrument 230 during an interventional procedure. Such slideable engagement may tend to prevent medical instrument 230 from moving in any direction with the exception of the direction desired for an interventional procedure, which may tend to provide additional accuracy for interventional procedures. In other embodiments, medical instrument support attachment 250 can hold medical instrument 230 in a fixed position during an interventional procedure, for example, using a strap or a locking device, which can tend to prevent medical instrument 230 from movement in any direction. It will be understood by those skilled in the art that medical instrument supports 252 may be designed specific to particular medical instruments such that for a particular medical instrument medical instrument support attachment 250 may have corresponding medical instrument supports 252 for slideable engagement which such particular medical instrument.

Medical instrument support attachment 250 may further comprise attachment arms 254 which may removeably engage fiducial holder slots 116 on guide plug holder 102 which may tend to securing medical instrument support attachment 250 in place during an interventional procedure.

Figure 15:
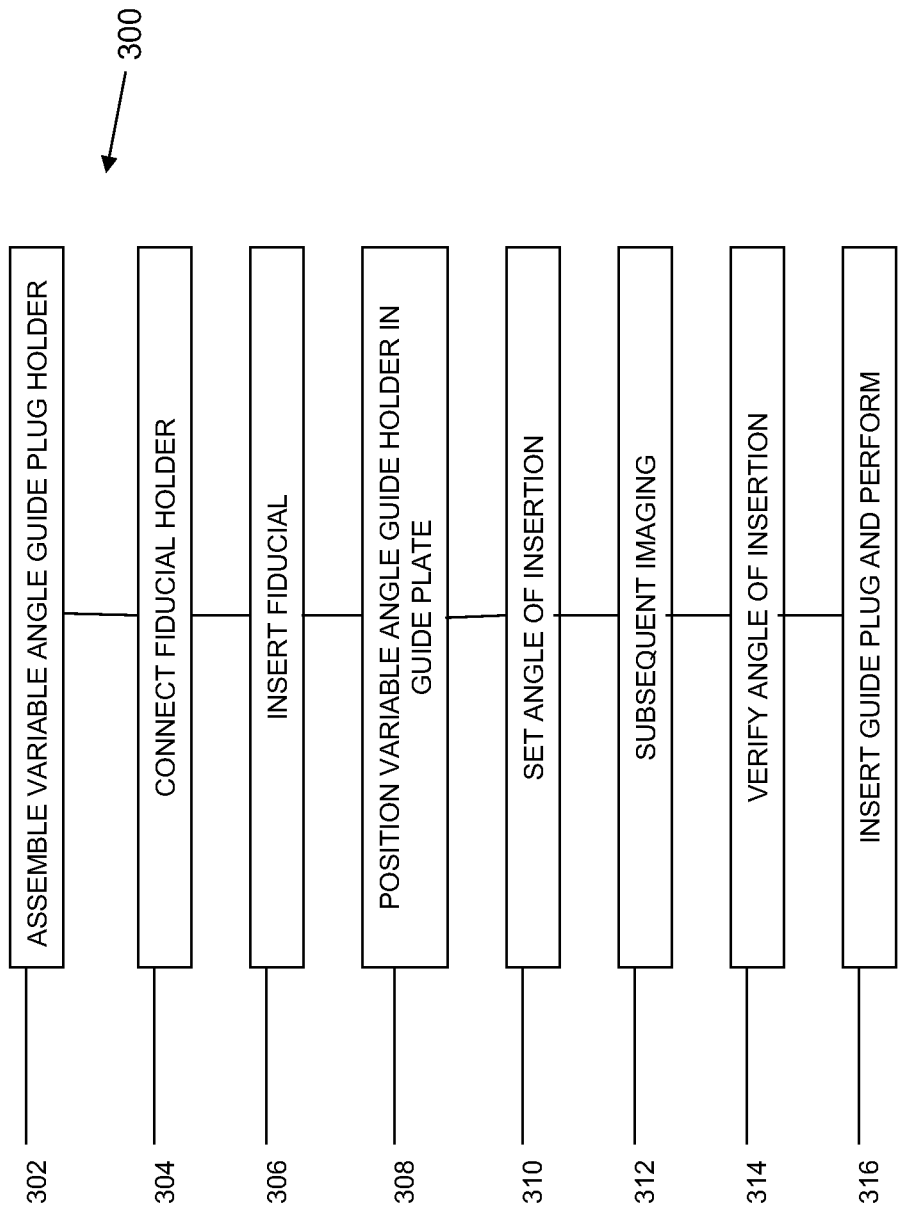
FIG. 15 shows a flow chart of a method of use of a variable angled guide plug holder in an intervention procedure.

Reference is now made to FIG. 15, where a use method 300 is shown illustrating the steps in one embodiment of using the variable angle guide plug holder 100 when performing an interventional procedure, such as a biopsy procedure, and, in some embodiments, when performing an image guided interventional procedure. Initially, a tissue of interest of a patient may be imaged, and such image may be examined to determine specific areas of interest within the tissue of interest for which it may be useful to perform an interventional procedure, such as a biopsy. It may tend to be found on this image that the areas of interest within a tissue may be inaccessible by certain paths through the tissue, for example, in a perpendicular path relative to a compression plate, compressing the tissue of interest during the image scanning procedure. Such blockages may be, for example, arteries, blood clots, or other tissue that may be difficult for a medical instrument 230 to pass through during an interventional procedure. In such embodiments it may tend to be useful to perform such interventional procedures from an angled point of entry, such that the elements blocking the area of interest in a tissue may be avoided.

Method 300 begins at step 302, where variable angle guide plug holder 100 is assembled. Upon assembly, method 300 proceeds to step 304, where fiducial holder 160 is connected to fiducial holder receptacles 116 on guide plug holder 102. Method 300 then proceeds to step 306, where fiducial 170 is inserted into fiducial holder 160 (see FIG. 10). Fiducial 160 can contain a fluid that can tend to be visible on an image obtained from an imaging scanning system, such as an MRI imaging system. In alternative embodiments, fiducial 160 may be comprised of a material that can tend to be visible on an image obtained from an imaging scanning system, such as an MRI imaging system.

With reference to FIG. 9, variable angle guide plug holder 100 may be positioned in guide plate 190 by inserting plate plug 150 into guide plate aperture 192 in step 308.

At step 310, based on the image obtained when the tissue of interest was scanned initially, variable angle guide plug holder 100 may be set to a desired angle by a user. For example, a user may position locking arm 120 into the unlocked position, slide guide plug holder 102 to the desired angle relative to angular determination fixture 130, and subsequently positioning locking arm 120 into the locked position, such that guide plug holder 102 may be prevented from additional movement relative to angular determination fixture 130.

At step 312, a subsequent imaging scan may be performed on the imaging system, such as an MRI imaging system. The subsequent scan can tend to obtain a subsequent image tending to show an image of the tissue of interest and an image of fiducial 170. This subsequent image may tend to provide information for a user to determine if the angle of insertion for which variable angle guide plug holder 100 is currently set, will likely provide the correct path such that a medical instrument 230 would be inserted towards and to a particular area of interest in the tissue of interest during an interventional procedure, such as a biopsy.

Upon the verification of the angle of insertion, method 300 proceeds to step 314, where fiducial holder 160 is removed, including fiducial 170. Method 300 proceeds to step 316, where guide plug 180 is inserted into plug securing mechanism 104 (see FIG. 11), such that a user may perform an interventional procedure on an area of interest within the tissue of interest by insertion of a medical instrument 230, such as a biopsy needle or a cannula, through guide aperture 182 of guide plug 180 (see FIG. 12).

The present invention has been described with regard to specific embodiments. However, it will be obvious to persons skilled in the art that a number of variants and modifications can be made without departing from the scope of the invention as described herein.

The invention claimed is:

1. A variable angle guide plug holder system for use in interventional procedures, comprising:
    a guide plug holder for receiving an angular determination fixture;
    the guide plug holder movable relative to the angular determination fixture between a plurality of positions, each position providing a different angle of insertion relative to a point of origin on the angular determination fixture;
    a plate plug engaged with the angular determination fixture;
    a guide plate having a plurality of guide plate apertures including a first guide plate aperture and a second guide plate aperture, wherein the plate plug is insertable into the first guide plate aperture;
    a locking arm connected to the guide plug holder, the locking arm movable between a locked and an unlocked position and removeably engageable with the angular determination fixture when positioned in the locked position to prevent movement of the guide plug holder relative to the angular determination fixture; and
    a medical instrument for use in an interventional procedure, configured to be inserted into the second guide plate aperture.

2. The variable angle guide plug holder system of claim 1, wherein a user may specify any angle of insertion between a first angle of insertion and a second angle of insertion.

3. The variable angle guide plug holder system of claim 2, wherein the guide plug holder further comprises fiducial holder receptacles for receiving a fiducial holder.

4. The variable angle guide plug holder system of claim 3, wherein the fiducial holder is able to receive a fiducial for verifying the angle of insertion during an image guided interventional procedure.

5. The variable angle guide plug holder system of claim 4, wherein the guide plug holder is moveable in an arched path relative to the angular determination fixture.

6. The variable angle guide plug holder system of claim 5, wherein the first angle of insertion is 89 degrees and the second angle of insertion is −89 degrees, relative to the point of origin.

7. The variable angle guide plug holder system of claim 5, wherein the first angle of insertion is 30 degrees and the second angle of insertion is −30 degrees, relative to the point of origin.

8. A variable angle guide plug holder system for use in interventional procedures, comprising:
    a guide plug holder having a groove for receiving a track connected to an angular determination fixture;
    the track slideable within the groove for moving the guide plug holder relative to the angular determination fixture in an arched path between a plurality of positions, each position providing a different angle of insertion relative to a point of origin on the angular determination fixture;
    a locking arm connected to the guide plug holder, the locking arm movable between a locked and an unlocked position and removeably engageable with an upper surface of the track when positioned in the locked position to prevent movement of the guide plug holder relative to the angular determination fixture;
    a plate plug engaged with the angular determination fixture;
    a guide plate having a plurality of guide plate apertures including a first guide plate aperture and a second guide plate aperture, wherein the plate plug is insertable into the first guide plate aperture; and
    a medical instrument for use in an interventional procedure, configured to be inserted into the second guide plate aperture.

9. The variable angle guide plug holder system of claim 8, wherein a user may specify any angle of insertion between a first angle of insertion and a second angle of insertion.

10. The variable angle guide plug holder system of claim 9, wherein the guide plug holder further comprises fiducial holder receptacles for receiving a fiducial holder.

11. The variable angle guide plug holder system of claim 10, wherein the fiducial holder is able to receive a fiducial for verifying the angle of insertion during an image guided interventional procedure.

12. The variable angle guide plug holder system of claim 11, wherein the first angle of insertion is 89 degrees and the second angle of insertion is −89 degrees, relative to the point of origin.

13. The variable angle guide plug holder system of claim 11, wherein the first angle of insertion is 30 degrees and the second angle of insertion is −30 degrees, relative to the point of origin.

14. A method of configuring a variable angle guide plug holder for the purpose of conducting an interventional procedure, comprising the steps of:
    determining an angle for insertion of a medical instrument for relative to a point of origin;
    inserting the variable angle guide plug holder into a first guide plate aperture of a plurality of guide plate apertures of a guide plate;
    setting the variable angle guide plug holder having a guide plug holder to the determined angle;
    inserting a guide plug into the guide plug holder;
    removeably engaging a locking arm of the guide plug holder into a locked position to prevent movement of the guide plug holder; and inserting a medical instrument through the guide plug and a second guide plate aperture of the plurality of guide plate apertures to a tissue of interest.

15. The method of configuring a variable angle guide plug holder of claim 14, further comprising the steps of:
   connecting a fiducial holder to the guide plug holder;
   inserting a fiducial through a fiducial aperture of the fiducial holder;
   imaging a patient using an imaging system to obtain an image displaying the tissue of interest and the fiducial;
   verifying the angle of insertion based on the image; and
   removing the fiducial holder from the guide plug holder.

16. The variable angle guide plug holder system of claim 1, further comprising:
   a guide plug mechanism connected to the guide plug holder; and
   a guide plug inserted in the guide plug mechanism, wherein the guide plug is configured to receive the medical instrument that is inserted through the guide plug mechanism to a tissue of interest.

17. The variable angle guide plug holder system of claim 16, wherein the guide plug mechanism comprises a guide plug aperture that is positioned to be aligned with the second guide plate aperture.

18. The variable angle guide plug holder system of claim 8, further comprising:
   a guide plug mechanism connected to the guide plug holder; and
   a guide plug inserted in the guide plug mechanism, wherein the guide plug is configured to receive the medical instrument that is inserted through the guide plug mechanism to a tissue of interest.

19. The variable angle guide plug holder system of claim 18, wherein the guide plug mechanism comprises a guide plug aperture that is positioned to be aligned with the second guide plate aperture.

* * * * *